US008198265B2

(12) United States Patent
Munn et al.

(10) Patent No.: US 8,198,265 B2
(45) Date of Patent: Jun. 12, 2012

(54) REGULATION OF T CELL-MEDIATED IMMUNITY BY TRYPTOPHAN

(75) Inventors: David Munn, Augusta, GA (US); Andrew Mellor, Augusta, GA (US)

(73) Assignee: Medical College of Georgia Research Institute Inc., Augusta, GA (US)

( * ) Notice: Subject to any disclaimer, the term of this patent is extended or adjusted under 35 U.S.C. 154(b) by 899 days.

(21) Appl. No.: 11/603,291

(22) Filed: Nov. 21, 2006

(65) Prior Publication Data

US 2007/0077234 A1    Apr. 5, 2007

Related U.S. Application Data

(62) Division of application No. 10/112,362, filed on Mar. 28, 2002, now Pat. No. 7,160,539, which is a division of application No. 09/206,274, filed on Dec. 4, 1998, now Pat. No. 6,451,840.

(60) Provisional application No. 60/067,610, filed on Dec. 5, 1997, provisional application No. 60/080,384, filed on Apr. 1, 1998, provisional application No. 60/080,380, filed on Apr. 1, 1998.

(51) Int. Cl.
*A61K 31/00* (2006.01)
*A61K 9/20* (2006.01)
*A61K 9/22* (2006.01)

(52) U.S. Cl. ........ 514/183; 424/451; 424/457; 424/463; 424/464

(58) Field of Classification Search .................. 514/183; 424/451, 457, 463, 464
See application file for complete search history.

(56) References Cited

U.S. PATENT DOCUMENTS

| | | | |
|---|---|---|---|
| 4,244,946 A | 1/1981 | Rivier et al. | |
| 4,305,872 A | 12/1981 | Johnston et al. | |
| 4,316,891 A | 2/1982 | Guillemin et al. | |
| 4,629,784 A | 12/1986 | Stammer | |
| 4,792,525 A | 12/1988 | Ruoslahti et al. | |
| 4,868,116 A | 9/1989 | Morgan et al. | |
| 4,980,286 A | 12/1990 | Morgan et al. | |
| 5,185,376 A * | 2/1993 | Diodati et al. ............. | 514/611 |
| 5,234,696 A * | 8/1993 | Van Scoik et al. .......... | 424/489 |
| 5,244,807 A | 9/1993 | Murtfeldt et al. | |
| 5,273,889 A * | 12/1993 | Potter et al. ............... | 435/69.51 |
| 5,478,556 A | 12/1995 | Elliott et al. | |
| 5,723,325 A | 3/1998 | Murtfeldt et al. | |
| 5,837,231 A | 11/1998 | Low et al. | |
| 5,861,159 A | 1/1999 | Pardoll et al. | |
| 5,874,560 A | 2/1999 | Kawakami et al. | |
| 5,879,707 A | 3/1999 | Cartilier et al. | |
| 6,251,399 B1 | 6/2001 | Diamond et al. | |
| 6,395,876 B1 | 5/2002 | Munn et al. | |
| 6,451,840 B1 | 9/2002 | Munn et al. | |
| 6,482,416 B2 | 11/2002 | Munn et al. | |
| 6,509,313 B1 * | 1/2003 | Smith ........................ | 514/2 |
| 7,160,539 B2 | 1/2007 | Munn et al. | |
| 7,465,448 B2 | 12/2008 | Munn et al. | |
| 7,598,287 B2 | 10/2009 | Munn et al. | |
| 2002/0114784 A1 | 8/2002 | Li et al. | |
| 2003/0194803 A1 | 10/2003 | Mellor | |
| 2004/0161425 A1 | 8/2004 | Munn | |
| 2004/0234623 A1 | 11/2004 | Munn | |
| 2005/0186289 A1 | 8/2005 | Munn | |
| 2006/0292618 A1 | 12/2006 | Mellor | |
| 2007/0048769 A1 | 3/2007 | Mellor | |
| 2007/0077234 A1 | 4/2007 | Munn et al. | |
| 2009/0081155 A1 | 3/2009 | Munn et al. | |
| 2009/0123420 A1 | 5/2009 | Munn et al. | |
| 2009/0155311 A1 | 6/2009 | Chen et al. | |
| 2009/0297540 A1 | 12/2009 | Mellor et al. | |

FOREIGN PATENT DOCUMENTS

| | | |
|---|---|---|
| EP | 0 385 385 A2 | 9/1990 |
| WO | WO 93/01286 | 1/1993 |
| WO | WO 98/25840 | 6/1998 |
| WO | WO 00/66764 | 11/2000 |
| WO | WO 2004/093871 A1 | 11/2004 |
| WO | WO 2004/094409 A1 | 11/2004 |
| WO | WO 2006/040796 | 10/2006 |
| WO | WO 2007/000404 | 1/2007 |
| WO | 2007/050405 | 5/2007 |

(Continued)

OTHER PUBLICATIONS

Musso et al. (1994) Blood, vol. 83, 1408-1411.*
Cady et al. (1991) Arch. Biochem. Biophys., vol. 291 (2), 326-333.*
Thomas et al. (1994) J. Biol. Chem., vol. 269 (2) 14457-14464.*
U.S. Appl. No. 12/083,855, filed Oct. 20, 2006, Mellor et al.
U.S. Appl. No. 12/158,170, filed Oct. 20, 2008, Chen et al.
U.S. Appl. No. 12/175,518, filed Jul. 18, 2008, Munn et al.
U.S. Appl. No. 12/175,538, filed Jul. 18, 2008, Munn et al.
Agrawal et al., "Oligodeoxynucleoside phosphoroamidates and phosphorothioates as inhibitors of human immunodeficiency virus", *Proc. Natl. Acad. Sci. USA*, 85:7079-7083 (1988).
Albertati-Giani et al., "Regulation of the Kynurenine Metabolic Pathway by Interferon-γ in Murine Cloned Macrophages and Microglial Cells", *J. Neurochem*, 66(3):996-1004 (1996).

(Continued)

*Primary Examiner* — Anne Marie S Wehbe
(74) *Attorney, Agent, or Firm* — Cooley LLP

(57) ABSTRACT

A mechanism of macrophage-induced T cell suppression is the selective elimination of tryptophan and/or increase in one or more tryptophan metabolites within the local macrophage microenvironment. Studies demonstrate that expression of IDO can serve as a marker of suppression of T cell activation, and may play a significant role in allogeneic pregnancy and therefore other types of transplantation, and that inhibitors of IDO can be used to activate T cells and therefore enhance T cell activation when the T cells are suppressed by pregnancy, malignancy or a virus such as HIV. Inhibiting tryptophan degradation (and thereby increasing tryptophan concentration while decreasing tryptophan metabolite concentration), or supplementing tryptophan concentration, can therefore be used in addition to, or in place of, inhibitors of IDO. Similarly, increasing tryptophan degradation (thereby, decreasing tryptophan concentration and increasing tryptophan metabolite concentration), for example, by increasing IDO concentration or IDO activity, can suppress T cells. Although described particularly with reference to IDO regulation, one can instead manipulate local tryptophan concentrations, and/or modulate the activity of the high affinity tryptophan transporter, and/or administer other tryptophan degrading enzymes. Regulation can be further manipulated using cytokines such as macrophage colony stimulating factor, interferon gamma, alone or in combination with antigen or other cytokines.

7 Claims, 6 Drawing Sheets

FOREIGN PATENT DOCUMENTS

| | | |
|---|---|---|
| WO | 2007/081878 | 7/2007 |
| WO | 2008/100562 | 8/2008 |

OTHER PUBLICATIONS

Albina et al., "Nitric Oxide Production is Required for Murine Resident Peritoneal Macrophages to Suppress Mitogen-Stimulated T Cell Proliferation", *J. Immunol.*, 147(1):144-148 (1991).

Alexander et al. "Indoleamine 2,3-Dioxygenase Expression in Transplanted NOD Islets Prolongs Craft Survival After Adoptive Transfer of Diabetogenic Splenocytes." *Diabetes*, vol. 51, Feb. 2002, pp. 356-365.

Almand et al., "Clinical Significance of Defective Dendritic Cell Differentiation in Cancer," *Clin. Cancer Res.*, 2000;6:1755-1766.

Askew et al., "Molecular Recognition with Convergent Functional Groups. 6. Synthetic and Structural Studies with a Model Receptor for Nucleic Acid Components", *J. Am. Chem. Soc.*, 111:1082-1090 (1989).

Asselin-Paturel et al., "Mouse type I IFN-producing cells are immature APCs with plasmacytoid morphology," *Nat. Immunol.*, 2001;2:1144-1150.

Attwood et al., "The Role of Tryptophan Depletion in T Cell Suppression by Macrophages", *Immunology*, 92(1):7, Abstract only (1997).

Aune et al., "Inhibition of Tumor Cell Growth by Interferon-γ Is Mediated by Two Distinct Mechanisms Dependent upon Oxygen Tension: Induction of Tryptophan Degradation and Depletion of Intracellular Nicotinamide Adenine Dinucleotide", *J. Clin. Invest*, 84:863-875 (1989).

Azuma et al., "B70 antigen is a second ligand for CTLA-4 and CD28", *Nature*, 366:76-79 (1993).

Bartlett et al. "Introduction of Immunomodulatory genes into isolated pancreatic islets via biolistic particle bombardment." *Transplant Proc.* Mar. 1998:30(2):452.

Baynes et al., "Lactoferrin and the Inflammatory Response", *Adv. Exp. Med. Biol.*, 357:133-141 (1994).

Begg et al., "Delayed Hematopoietic Development in Osteopetrotic (op/op) Mice", *J. Exp. Med.*, 177:237-242 (1993).

Belongia et al., "An Investigation of the Cause of the Eosinophilia-Myalgia Syndrome Associated with Tryptophan Use", *The New England Journal of Medicine*, 323(6):357-365 (1990).

Ben-Efraim, "Immunomodulating Anticancer Alkylating Drugs: Targets and Mechanisms of Activity," *Current Drug Targets*, 2001;2:197-212.

Benson et al., "T-cell activation and receptor downmodulation precede deletion induced by mucosally administered antigen," *J. Clin. Invest.*, 2000;106:1031-1038.

Berney et al., "Transplantation of islets of Langerhans: new developments." *Swiss Med Wkly* 2002; 132:671-680.

Beutelspacher et al., "Function of indoleamine 2,3-dioxygenase in corneal allograft rejection and prolongation of allograft survival by over-expression," 2006. *Eur. J. Immunol.* 36:690-700.

Bjorck et al., "Cutting Edge: CD19+ Pro-B Cells Can Give Rise to Dendritic Cells In Vitro," *J. Immunol.*, 1998; 161:5795-5799.

Bliznakov, "Serotonin and its precursors as modulators of the immunological responsiveness in mice", *Journal of Medicine*, 11:81-105 (1980).

Blume et al., "Triple Helix Formation by Purine-rich Oligonucleotides Targeted to the Human Dihydrofolate Reductase Promoter", *Nucl. Acids Res.*, 20:1777-1784 (1992).

Bock et al., eds., "Polyfunctional Cytokines: IL-6 and LIF", *Ciba Foundation Symposium 167*, Title page and Table of Contents (1992).

Bock et al., eds., "Interactions Among Cell Signalling Systems", *Ciba Foundation Symposium 164*, Title page and Table of Contents (1992).

Bogdan, "The Multiplex Function of Nitric Oxide in (Auto)immunity", *J. Exp. Med.*, 187(9):1361-1365 (1998).

Bonney et al., "Much IDO about pregnancy", *Nature Medicine*, 4(10):1128-1129 (1998).

Borrello et al., "A Universal Granulocyte-Macrophage Colony-Stimulating Factor-Producing Bystander Cell Line for Use in the Formulation of Autologous Tumor Cell-Based Vaccine," *Hum. Gene. Ther.*, 1999;10:1983-1991.

Brás et al., "Nitric Oxide Regulates Clonal Expansion and Activation-Induced Cell Death Triggered by Staphylococcal Enterotoxin B", *Infection and Immunity*, 65(10):4030-4037 (1997).

Bronte et al., "Unopposed Production of Granulocyte-Macrophage Colony-Stimulating Factor by Tumors Inhibits CD8+ T Cell Responses by Dysregulating Antigen-Presenting Cell Maturation," *J. Immunol.*,1999;162:5728-5737.

Burke et al., "The role of indoleamine 2,3-dioxygenase in the antitumor activity of human interferon-gamma in vivo", *Int. J. Cancer*, 60(1):115-122 (1995).

Cady et al., "1-Methyl-DL-tryptophan, β-(3-Benzofuranyl)-DL-alanine (the Oxygen Analog of Tryptophan), and β-[3-Benzo(b)thienyl]-DL-alanine (the Sulfur Analog of Tryptophan) Are Competitive Inhibitors for Indoleamine 2,3-Dioxygenase", *Arch. Biochem. Biophys.*, 291(2):326-333 (1991).

Capecchi, Ed., "Molecular Genetics of Early Drosophila and Mouse Development", *Current Communications in Molecular Biology*, Cold Spring Harbor Laboratory Press, Title page and Table of Contents (1989).

Carlin et al., "Interferon-Induced Indoleamine 2,3-Dioxygenase Activity in Human Mononuclear Phagocytes", *Journal of Leukocyte Biology*, 45:29-34 (1989).

Casciari et al., "Glucose Diffusivity in Multicellular Tumor Spheroids", *Cancer Research*, 48:3905-3909 (1988).

Cecchini et al., "Role of colony stimulating factor-1 in the establishment and regulation of tissue macrophages during postnatal development of the mouse", *Development*, 120:1357-1372 (1994).

Cella et al., "Plasmacytoid monocytes migrate to inflamed lymph nodes and produce large amounts of type I interferon," *Nat. Med.*, 1999;5:919-923.

Chapman et al., "Pharmacologically Active Benzol[b]thiophen Derivatives. Part VIII. Benzo[b]thiophen analogues of Tryptophan and α-Methyltryptophan, and Some of their 5-Substituted Derivatives", *J. Chem. Soc. (C)*, 14:1855-1858 (1969).

Chambers, "The expanding world of co-stimulation: the two-signal model revisited," *Trend Immunol.* 2001;22:217-223.

Chen et al., Eradication of Murine Bladder Carcinoma by Intratumor Injection of Bicistronic Adenoviral Vector Carrying cDNAs for the IL-12 Heterodimer and Its Inhibition by the IL-12 p40 Subunit Homodimer, *The Journal of Immunology*, 159:351-359 (1997).

Chen et al., "The Role of Tumor Necrosis Factor α in Modulating the Quantity of Peripheral Blood-Derived, Cytokine-Driven Human Dendritic Cells and Its Role in Enhancing the Quality of Dendritic Cell Function in Presenting Soluble Antigens to CD4+ T Cells in Vitro," *Blood*, 1998;91:4652-4661.

Cheng et al., "Relationship Between the Inhibition Constant ($K_1$) and the Concentration of Inhibitor Which Causes 50 Per Cent Inhibition ($I_{50}$) of an Enzymatic Reaction", *Biochemical Pharmacology*, 22:3099-3108 (1973).

Chon et al., "Cooperative Role of Interferon Regulatory Factor 1 and p91 (STAT1) Response Elements in Interferon-γ-inducible Expression of Human Indoleamine 2,3-Dioxygenase Gene", *J. Biol. Chem.*, 271(29):17247-17252 (1996).

Cicala et al., "NO-naproxen modulates inflammation, nociception and downregulates T cell response in rat Freund's adjuvant arthritis", *British Journal of Pharmacology*, 130(6):1399-1405 (2000).

Cochran et al., "Sentinel Lymph Nodes Show Profound Downregulation of Antigen-Presenting Cells of the Pracortex: Implications for Tumor Biology and Treatment," *Mod. Pathol.*, 2001;14:604-608.

Colasante et al., "Role of Cytokines in Distribution and Differentiation of Dendritic Cell/Langerhans' Cell Lineage in Human Primary Carcinomas of the Lung," *Hum. Pathol.*, 1995;26:866-872.

Cooney et al., "Site-Specific Oligonucleotides Binding Represses Transcription of the Human c-myc Gene in Vitro", *Science*, 241:456-459 (1988).

Corbett et al., "Response of Transplantable Tumors of Mice to Anthracenedione Derivatives Alone and in Combination with Clinically Useful Agents," *Cancer Treatment Reports*, 1982;66:1187-1200.

Corcoran et al.,"The lumphoid Past of Mouse Plasmacytoid Cells and Thymic Dendritic Cells," *J. of Immunology*, 2003;170:4926-4932.

Crook; "Progress Toward Oligonucleotide Therapeutics: Pharmacodynamic Properties", *FASEB J.*, 7:533-539 (1993).

Cuenca et al., "Extra-Lymphatic Solid Tumor Growth Is Not Immunologically Ignored and Results in Early Induction of Antigen-Specific T-Cell Anergy: Dominant Role of Cross-Tolerance to Tumor Antigens," *Cancer Res.*, 2003;63:9007-9015.

Currelli et al., "Human Primary CD4+ T Cells Activated in the Presence of IFN-α2b Express Functional Indoleamine 2,3-Dioxygenase," *J. Interferon Cytokine Res.*, 2001;21:431-437.

Dai et al., "Molecular Cloning, Sequencing and Expression of Human Interferon-γ-Inducible Indoleamine 2,3-Dioxygenase cDNA", *Biochemical and Biophysical Research Communications*, 168(1):1-8 (1990).

Dalton et al., "Multiple Defects of Immune Cell Function in Mice with Disrupted Interferon-γ Genes", *Science*, 259:1739-1742 (1993).

Däubener et al., "Establishment of T-helper type 1- and T-helper type 2-like human *Toxoplasma* antigen-specific T-cell clones", *Immunology*, 86:79-84 (1995).

Däubener et al., "Anti-parasitic effector mechanisms in human brain tumor cells: role of interferon-γ and tumor necrosis factor-α", *Eur. J. Immunol*, 26:487-492 (1996).

Degauque et al., "Dominant Tolerance to Kidney Allografts Induced by Anti-Donor MHC Class II Antibodies: Cooperation between T and Non-T CD 103+ Cells," 2006. *Journ. Of Immunology*. pp. 3915-3922.

Dong et al., "Activation of CFTR chloride current by nitric", *EMBO J.*, 14(12): 2700-2707 (1995). Abstract only (1 pg.).

Dranoff, "GM-CSF-based cancer vaccines," *Immunol. Rev.* 2002;188:147-154.

Dranoff et al., "Vaccination with irradiated tumor cells engineered to secrete murine granulocyte-macrophage colony-stimulating factor stimulates potent, specific, and long-lasting anti-tumor immunity," *Proc. Natl. Acad. Sci. USA*, 1993;90:3539-3543.

Dudley et al., "Cancer Regression and Autoimmunity in Patients After Clonal Repopulation with Antitumor Lymphocytes," *Science*, 2002;298:850-854. Supplemental On-line Material can be retrieved from www.sciencemag.org/cqi/content/full/1076514/DC1.

Duval-Valentin et al., "Specific Inhibition of Transcription by Triple Helix-Forming Oligonucleotides", *Proc. Natl. Acad. Sci. USA*, 89:504-508 (1992).

Dzionek et al., "BDCA-2, BDCA-3, and BDCA-4: Three Markers for Distinct Subsets of Dendritic Cells in Human Peripheral Blood," *J Immunol.*, 2000;165:6037-6046.

Efron et al., "Nitric oxide generation from L-arginine is required for optimal human peripheral blood lymphocyte DNA synthesis", *Surgery*, 110:327-334 (1991).

Ellington et al., "In vitro selection of RNA molecules that bind specific ligands," *Nature*, Aug. 30, 1990;346(6287):818-22.

Ellington et al., "Selection in vitro of single-stranded DNA molecules that fold into specific ligand-binding structures", *Nature*, 355(6363):850-852 (1992).

Fallarino et al., "Functional expression of indoleamine 2,3-dioxygenase by murine CD8α+ dendritic cells," *Int. Immunol.*, 2002;14:65-68.

Fallarino et al., "Modulation of tryptophan catabolism by regulator T cells," *Nat. Immunol.*, 2003;4:1206-1212. Epub Oct. 26, 2003.

Fearon et al., "The Instructive Role of Innate Immunity in the Acquired Immune Response", *Science*, 272:50-54 (1996).

Feng et al., "Interferon γ-resistant mutants are defective in the induction of indoleamine 2,3-dioxygenase", *Proc. Natl. Acad. Sci. USA*, 86:7144-7148 (1989).

Fleckner et al., "Human interferon γ potently induces the synthesis of a 55-kDa protein (γ2) highly homologous to rabbit peptide chain release factor and bovine tryptophanyl-tRNA synthetase", *Proc. Natl. Acad. Sci. USA*, 88(24):11520-11524 (1991).

Fleckner et al., "Differential Regulation of the Human, Interferon Inducible Tryptophanyl-tRNA Synthetase by Various Cytokines in Cell Lines", *Cytokine*, 7(1):70-77 (1995).

Friberg et al., "Indoleamine 2,3-dioxygenase contributes to tumor cell evasion of T cell mediated rejection," *Intl J of Cancer*, 2002;101:151-155.

Giannoukakis et al. "Targeting Autoimmune Diabetes with Gene Therapy." *Diabetes*, vol. 48, Nov. 1999, pp. 2107-2121.

Giannoukakis et al. "Prevention of beta cell dysfunction and apoptosis activation in human islets by adenoviral gene transfer of the insulin-like growth factor I." *Gene Ther* Dec. 2000;7(23):2015-22.

Giannoukakis et al. "Infection of intact human islets by a lentiviral vector." *Gene Ther* Sep. 1999;6(9):1545-51.

Giannoukakis et al., "Adenoviral Gene Transfer of the Interleukin-1 Receptor Antagonist Protein to Human Islets Prevents IL-1β-Induced β-Cell Impairment and Activation of Islet Cell Apoptosis in Vitro." *Diabetes*, vol. 48, Sep. 199, pp. 17301736.

Gmünder et al., "Macrophages Regulate Intracellular Glutathione Levels of Lymphocytes. Evidence for an Immunoregulatory Role of Cysteine", *Cell. Immunol.*, 129:32-46 (1990).

Grant et al., "Induction of Indolamine 2,3-Dioxygenase in Primary Human Macrophages by Human Immunodeficiency Virus Type 1 Is Strain Dependent," *J. Virol.*, 2000;74:4110-4115.

Grigoriev et al., "A Triple Helix-forming Oligonucleotide-Intercalator Conjugate Acts as Transcriptional Repressor via Inhibition of NF KB Binding to Interleukin-2 Receptor α-Regulatory Sequence", *J. Biol. Chem.*, 267:3389-3395 (1992).

Grohmann et al., "IL-6 Inhibits the Tolerogenic Function of CD8α+ Dendritic Cells expressing Indoleamine 2,3-Dioxygenase," *J. Immunol.* 2001;167:708-714.

Grohmann et al., "CD40 Ligation Ablates the Tolerogenic Potential of Lymphoid Dendritic Cells," *J. Immunol.* 2001;166:277-283.

Grohmann et al., "CTLA-4-1g regulates tryptophan catabolism in vivo," *Nat. Immunol.*, Nov. 2002;3(11):1097-1101. Epub Sep. 30, 2002. pp. 1-5.

Grohmann at al., "Tolerance, Dcs and tryptophan: much ado about IDO," *Trends in Immunology* 2003;24:242-248.

Grohmann et al., "A Defect in Tryptophan Catabolism Impairs Tolerance in Nonobese Diabetic Mice," *J. Exp. Med.* 2003;198:153-160.

Gupta et al., "Antiparasitic and antiproliferative effects of indoleamine 2,3-dioxygenase enzyme expression in human fibroblasts", *Infect. Immun*, 62:2277-2284 (1994).

Gura, "Systems for Identifying New Drugs are Often Faulty," *Science*, 1997, 278:1041-1042.

Habara-Ohkubo et al., "Cloning and expression of a cDNA encoding mouse indoleamine 2,3-dioxygenase", *Gene*, 105(2):221-227 (1991).

Habara-Ohkubo et al. "Establishment of an Antitoxoplasma State by Stable Expression of Mouse Indoleamine 2,3-Dioxygenase." *Infection and Immunity*, May 1993, vol. 61, No. 5, pp. 1810-1813.

Hashimoto et al., "Determination of free amino acid enantiomers in rat brain and serum by high-performance liquid chromatography after derivatization with N-*tert.*-butyloxycarbonyl-L-cysteine and o-phthaldialdehyde," *J. Chromatography* 1992;582:41-48.

Haspot et al., "Anti-CD28 Antibody-Induced Kidney Allograft Tolerance Related to Tryptophan Degradation and TCR—Class II—B7+ Regulatory Cells," 2005. *Amer. Journ. Of Transplantation*, 5:2339-2348.

Hawiger et al., "Dendritic Cells Induce Peripheral T Cell Unresponsiveness Under Steady State Conditions in Vivo," *J. Exp. Med.*, 2001;194:769-779.

Hayaishi, "Utilization of Superoxide Anion by Indoleamine Oxygenase-Catalyzed Tryptophan and Indoleamine Oxidation", *Adv. Exp. Med. Biol.*, 398:285-289 (1996).

Heesen et al., "β$_2$-Adrenoceptor Density of Human Lymphocytes After Nitroprusside-Induced Hypotension", *Anesth Analg*, 81:1250-1254 (1995).

Hogan et al., "Manipulating the Mouse Embryo—A Laboratory Manual", *Cold Spring Harbor Laboratory*, 1 pg. publication (1986).

Holt et al., "An Oligomer Complementary to c-myc mRNA Inhibits Proliferation of HL-60 Promyelocytic Cells and Induces Differentiation", *Mol. Cell. Biol.*, 8:963-973 (1988).

Hou et al., "Inhibition of indoleamine 2,3-dioxygenase in dendritic cells by stereoisomers of 1-methyl-tryptophan correlates with anti-tumor responses," *Cancer. Res.* Jan. 15, 2007;67(2):792-801.

Huang et al., "Role of Bone Marrow-Derived Cells in Presenting MHC Class I-Restricted Tumor Antigens," *Science*, 1994;264:961-965.

Hwu et al., "Indoleamine 2,3-Dioxygenase Production by Human Dendritic Cells Results in the Inhibition of T Cell Proliferation," *J. Immunol.* 2000;164:3596-3599.

Ibrahim et al., "The injured cell: the role of the dendritic cell system as a sentinel receptor pathway", *Immunology Today*, 16(4):181-186 (1995).

Itakura et al., "Synthesis and use of Synthetic Oligonucleotides", *Ann. Rev. Biochem.*, 53:323-356 (1984).

Iwata et al., "Thiol-Mediated Redox Regulation of Lymphocyte Proliferation. Possible Involvement of Adult T Cell Leukemia-Derived Factor and Glutathione in Transferrin Receptor Expression", *J. Immunol.*, 152:5633-5642 (1994).

Izon et al., "A Common Pathway for Dendritic Cell and Early B Cell Development," *J. Immunol.*, 2001;167:1387-1392.

Janeway, Jr., "The immune system evolved to discriminate infectious nonself from noninfectious self", *Immunology Today*, 13(1):11-16 (1992).

Janeway, Jr. et al., *ImmunoBiology, The Immune System in Health and Disease*, Current Biology Limited, London, U.K., 12:30-12:34 (1994).

Johnson et al., "Relationships between drug activity in NCI preclinical in vitro and in vivo models and early clinical trials," *British Journal of Cancer*, 2001, 84(10):1424-1431.

Jonuleit et al., "Pro-inflammatory cytokines and prostaglandins induce maturation of potent immunostimulatory dendritic cells under fetal calf serum-free conditions," *Eur. J. Immunol.*, 1997;27:3135-3142.

Jorgensen et al., "Gene therapy in osteoarticular diseases: where are we?", *Immunology Today*, 19(9):387-391 (1998).

Kadoya et al., "Gene structure of human indoleamine 2,3-dioxygenase," *Bio. and Biophysical Research Comm.* 1992, vol. 189, No. 1 pp. 530-536.

Kakuda et al., "Na(+)-independent transport (uniport) of amino acids and glucose in mammalian cells", *J. Exp. Biol.*, 196:93-108 (1994).

Kamijo et al., "Mice That Lack the Interferon-γ Receptor Have Profoundly Altered Responses to Infection with Bacillus Calmette-Guérin and Subsequent Challenge with Lipopolysaccharide", *J. Exp. Med.*, 178:1435-1440 (1993).

Kamimura et al., "Localization and Developmental Change of Indoleamine 2,3-Dioxygenase Activity in the Human Placenta", *Acta Med Okayama*, 45(3):135-139 (1991).

Kamath et al., "Amino Acid-Restricted Diets in the Treatment of Mammary Adenocarcinoma in Mice", *J. Nutr.*, 118(9):1137-1142 (1988).

Kapturczak et al. "Transduction of human and mouse pancreatic islet cells using a bicistronic recombinant adeno-associated viral vector." *Mol Ther* Feb. 2002;5(2):154-160.

Karsunky et al., "Flt3 Ligand Regulates Dendritic Cell Development from Flt3+ Lymphoid and Myeloid-committed Progenitors to Flt3+ Dendritic Cells In Vivo," *J. Exp. Med.*, 2003;198:305.

Kaufman et al. (1995) "Xenotransplantation," *Annu. Rev. Immnol.*, vol. 13:339-367.

Kenyon et al. "Islet transplantation; present and future perspectives." *Diabetes Metab Rev* Dec. 1998;14(4)303-313.

Kisselev, "Mammalian tryptophanyl-tRNA synthetases", *Biochimie*, 75:1027-1039 (1993).

Koide et al., "The Signal Transduction Mechanism Responsible for Gamma Interferon-Induced Indoleamine 2,3-Dioxygenase Gene Expression",*Infection and Immunity*, 62(3):948-955 (1994).

Kolb et al., "Nitric oxide in autoimmune disease: cytotoxic or regulatory mediator?", *Immunology Today*, 19(12): 556-561 (1998).

Konan, "Importance of the Two Interferon-stimulated Response Element (ISRE) Sequences in the Regulation of the Human Indoleamine 2,3-Dioxygenase Gene," *J. Biol. Chem.*, 271:19140-19145 (1996).

Konieczny et al., "IFN-γ Is Critical for Long-Term Allograft Survival Induced by Blocking the CD28 and CD40 Ligand T Cell Costimulation Pathways," *J. Immunol.*, 1998;160:2059.

Kotera et al., "Comparative Analysis of Necrotic and Apoptotic Tumor Cells As a Source of Antigen(s) in Dendritic Cell-based Immunization," *Cancer Research* 2001;61(22):8105-8109.

Kudo et al., "Human placental indoleamine 2,3-dioxygenase: cellular localization and characterization of an enzyme preventing fetal rejection," *Biochem. Biophys. Acta*, 2000;1500:119-124.

Lee et al., "Pattern of Recruitment of Immunoregulatory Antigen-Presenting Cells in Malignant Melanoma," *Laboratory Investigation*, 2003;83:1457-1466.

Lee et al., "Tryptophan deprivation sensitizes activated T cells to apoptosis prior to cell division," *Immunology* 2002;107:452-460.

Li et al., "Expression of indoleamine 2,3-dioxygenase in dermal fibroblasts functions as a local immunosuppressive factor," *J. Invest. Dermatol.* 2004, 122(4):953-964.

Logan et al., "Potential Use of Genetically Modified Pigs as Organ Donors for Transplantation into Humans," *Clinical and Exper. Pharm. and Physiology* (1999) 26, 1020-1025.

Logan et al., "HeLa cells cocultured with peripheral blood lymphocytes acquire an immuno-inhibitory phenotype through up-regulation of indoleamine 2,3-dioxygenase activity," *Immunol.*, 2002;105:478.

Mackensen et al., "Delineation of the Dendritic Cell Lineage by Generating Large Numbers of Birbeck Granule-Positive Langerhans Cells from Human Peripheral Blood Progenitor Cells in Vitro," 1995, *Blood*, 86:2699-2707.

MacMicking et al., "Nitric Oxide and Macrophage Function", *Annu. Rev. Immunol.*, 15:323-350 (1997).

Maher et al., "Inhibition of DNA binding proteins by oligonucleotide-directed triple helix formation", *Science*, 245:725-730 (1989).

Manegold et al., "Gemcitabine in non-small cell lung cancer (NSCLC)", *Invest New Drugs.* 2000;18(1):29-42.

Martin et al., "Characterization of a new subpopulation of mouse $CD8\alpha^+ B220^+$ dendritic cells endowed with type 1 interferon production capacity and tolerogenic potential," *Blood*, 2002;100:383-390.

Mattei et al., "Expression of Cytokine/Growth Factors and Their Receptors in Human Melanoma and Melanocytes," *Int. J. Cancer*, 1994;56:853-857.

Mayeno et al., "Characterization of "Peak," a Novel Amino Acid Associated with Eosinophilia-Myalgia Syndrome", *Science*, 250:1707-1708 (1990).

McGivan et al., "Regulatory and molecular aspects of mammalian amino acid transport", *Biochem J.*, 299(Part 2):321-334 (1994).

McIlroy et al., "Investigation of human spleen dendritic cell phenotype and distribution reveals evidence of in vivo actibation in a subset of organ donors," *Blood*, 2001; 97:3470-3477.

McKinlay et al., "Rational Design of Antiviral Agents", *Annu. Rev. Pharmacol. Toxicol.*, 29:111-122 (1989).

Medawar, "Some Immunological and Endocrinological Problems Raised by the Evolution of Viviparity in Vertebrates", *Symp. Soc. Exp. Biol.*, 7:320-328 (1953).

Mellor et al., "Tryptophan catabolism and T-cell tolerance: immunosuppression by starvation?", *Immunology Today*, 20(10):469-473 (1999).

Mellor et al., "HLA-G transgenic mice", *Journal of Reproductive Immunology*, 43:253-261 (1999).

Mellor et al., Immunology at the Maternal-Fetal Interface: Lessons for T Cell Tolerance and Suppression, *Annu. Rev. Immunol*, 18:367-391 (2000).

Mellor et al., "Prevention of T cell-driven complement activation and inflammation by tryptophan catabolism during pregnancy",*Nature Immunology*, 2(1):64-68 (2001).

Mellor et al. "Cells Expressing Indoleamine 2,3-Dioxygenase Inhibit T Cell Responses." *IDO and T Cell Responses*. 2002 , pp. 3771-3776.

Mellor et al., "Cutting edge: CpG Oligonucleotides Induce Spenic CD19+ Dendritic Cells to Acquire Potent Indoleamine 2,3-Dioxygenase-Dependent T Cell Regulatory Functions via IFN Type 1 Signaling," *Journ. Of Immun.* 2005. pp. 5601-5605.

Mellor et al., "Prevention of T cell-driven complement activation and inflammation by Tryptophan catabolism during pregnancy," *Nature Immunol.* 2001;2:64-68.

Mellor et al., "Indoleamine 2,3-dioxygenase, immunosuppression and pregnancy," *J. Reprod. Immunol.* 2002;57:143-150.

Mellor et al., "Tryptophan catabolism and regulation of adaptive immunity," J. Immunol. 2003;170:5809-5813.

Merrifield, "Solid Phase Peptide Synthesis. I. The Synthesis of a Tetrapeptide", *J. Am. Chem. Soc.*, 85:2149-2154 (1963).

Meyer et al., "Trptophan metabolism in chronic inflammatory lung disease",*J. Lab. Clin. Med.*,126(6):530-540 (1995).

Miki et al., "Blockade of Tryptophan Catabolism Prevents Spontaneous Tolerogenicity of Liver Allografts" *Transplantation Proceedings* 2001;33:129-130.

Miki et al., Abstract # 714, "Indoleamine 2, 3-Dioxygenase Blockade Prevents Spontaneous Liver Allograft Tolerogenicity in the Mouse", *Transplantation®*, 69(8):S297 (2000).

Mikkola et al., "Reversion of B Cell Commitment Upon Loss of Pax5 Expression," *Science*, 2002;297:110-113.

Mills, "Molecular Basis of "Suppressor" Macrophages—Arginine Metabolism via the Nitric Oxide Synthetase Pathway", *J. Immunol.*, 146(8):2719-2723 (1991).

Moffett et al., "Antibodies to quinolinic acid and the determination of its cellular distribution within the rat immune system", *Cell Tissue Res.*, 278:461-469 (1994).

Mondino et al., "The anatomy of T-cell activation and tolerance", *Proc. Natl. Acad. Sci. USA*, 93:2245-2252 (1996).

Moore et al., "Enhanced Response of Macrophages to CSF-1 in Autoimmune Mice", *J. Immunol*, 157:433-440 (1996).

Morahan et al., "Macrophage Heterogencity", *Macrophages and Cancer*, pp. 1-25 (Heppner G.H., Fulton A.M., eds.) CRC Press: Boca Raton, FL (1988).

Morgan et al., "Scleroderma and autoimmune thrombocytopenia associated with ingestion of L-tryptophan", *British Journal fo Dermatology*, 128:581-583 (1993).

Moser, "Dendritic Cells in Immunity and Tolerance—Do They Display Opposite Functions?" *Immunity*, 2003;19:5-8.

Muller et al., "Indoleamine 2,3-dioxygenase in cancer: targeting pathological immune tolerance with small-molecule inhibitors," *Expert Opinion Ther. Targets*, 2005, 9(4):831-849.

Mulligan, "The Basic Science of Gene Therapy", *Science*, 260:926-932 (1993).

Munn et al., "Antibody-Dependent Antitumor Cytotoxicity by Human Monocytes Cultured with Recombinant Macrophage Colony-Stimulating Factor", *J. Exp. Med.*, 170:511-526 (1989).

Munn et al., "Cytokine Regulation of Human Monocyte Differentiation in Vitro: The Tumor-Cytotoxic Phenotype Induced by Macrophage Colony-stimulating Factor Is Developmentally Regulated by γ-Interferon", *Cancer Research*, 53:2603-2613 (1993).

Munn, David H., "Regulation of Macrophage Apoptosis," Grant Abstract, Grant No. 1K08HL03395-01 [online]. National Institutes of General Medical Sciences, National Institutes of Health, project dates Jul. 1, 1995-Jun. 30, 1998 [retrieved on Feb. 15, 2001]. Retrieved from the Internet: URL: http.commons.cit.nih.gov/crisp_historical/crisp_lib.getdoc?textkey=2211646&p_grant_num=1K08HL03395-01&p_query=&ticket=63957&p_audit_session_id=363938&p_keywords=>, 2 pages.

Munn et al., "Selective Activation-Induced Apoptosis of Peripheral T Cells Imposed by Macrophages", *The Journal of Immunology*, 156:523-532 (1996).

Munn, David H., "Inhibition of T Cells by Tryptophan Degradation," Grant Abstract, Grant No. 1R21AI44759-01 [online]. National Institutes of General Medical Sciences, National Institutes of Health, project dates Sep. 30, 1998-Sep. 29, 2000 [retrieved on Feb. 15, 2001]. Retrieved from the Internet: URL: http.commons.cit.nih.gov/crisp_historical/crisp_lib.getdoc?textkey=2802812&p_grant_num=IR21AI44759-01&p_query=&ticket=63957&p_audit_session_id=363938&p_keywords=>, 2 pages.

Munn et al., "Prevention of Allogeneic Fetal Rejection by Tryptophan Catabolism", *Science*, 281:1191-1193 (1998).

Munn et al., "Inhibition of T Cell Proliferation by Macrophage Tryptophan Catabolism", *J. Exp. Med.*, 189(9):1363-1372 (1999).

Munn, David H., "Macrophage Mediated Immunoregulation Via Tryptophan," Grant Abstract, Grant No. 5R01HL60137-03 [online]. National Institutes of General Medical Sciences, National Institutes of Health, project dates Jan. 1, 1999-Dec. 31, 2002 [retrieved on Feb. 15, 2001]. Retrieved from the Internet: URL: http.commons.cit.nih.gov/crisp_lib.getdoc?textkey=6343616&p_query=&ticket=1890054&p_audit_session_id=3588259&p_keywords=>, 2 pages.

Munn et al., Basic Aspects of Tumor Immunology "Dendritic cells (Dcs) expressing indoleamine 2,3-dioxygenase (IDO) in malignancy," Basic Aspects of Tumor Immunology. Abstract No. 346, Keystone Symposium, 2003 Abstract Book, p. 107, Keystone Resort, Keystone, Colorado, Feb. 17-23, 2003.

Munn et al., "Potential regulatory function of human dendritic cells expressing indoleamine 2,3-dioxygenase," *Science*, 2002;297:1867-1870. Supporting On-Line Material available at www.sciencemag.org/cgi/data/297/5588/1867/DC1/1.

Munn, "Selecting the right dentritic cell subset," Lecture Presented Jan. 31, 2003 at Tandem BMT Meetings at Keystone. Jan. 30-Feb. 3, 2003, 57 pages.

Munn, "Indoleamine 2,3-dioxygenase, tumor-induced tolerance and counter-regulation," *Curr. Opin. Immunol.* Apr. 2006;18(2):220-225. Epub Feb. 7, 2006.

Munn et al., "Expression of indoleamine 2,3-dioxygenase by plasmacytoid dendritic cells in tumor-draining lymph nodes," *J. Clin Invest* 2004;114:280-290.

Munn et al., "IDO and tolerance to tumors," *Trends Molec Med.* 2004;10:15-18.

Musso et al., "Interleukin-4 Inhibits Indoleamine 2,3-Dioxygenase Expression in Human Monocytes", *Blood*, 83(5):1408-1411 (1994).

Nagineni et al., "Mechanisms of Interferon-Induced Inhibition of *Toxoplasma gondii* Replication in Human Retinal Pigment Epithelial Cells", *Infection and Immunity*, 64(10):4188-4196 (1996).

Narang et al., "[61] Chemical Synthesis of Deoxyoligonucleotides by the Modified Triester Method", *Methods in Enzymology*, 65:610-620 (1980).

Nguyen et al., "Tumor Growth Enhances Cross-Presentation Leading to Limited T Cell Activation without Tolerance," *J. Exp. Med.*, 2002;195:423-435.

Nossal, "Negative Selection of Lymphocytes" *Cell*, 76:229-239 (1994).

Nowak et al., "Synergy between Chemotherapy and Immunotherapy in the Treatment of Established Murine Solid Tumors," *Cancer Research* 2003;63:4490-4496.

Nutt et al., "Identification of BSAP (Pax-5) target genes in early B-cell development by loss- and gain-of-function experiments," *EMBO J.*, 1998;17:2319-2333.

Nutt et al., "Committment to the B-lymphoid lineage depends on the transcription factor Pax5," *Nature*, 1999;401:556-562.

Oettle, et al., "Phase I Trial of gemcitabine (Gemzar(, 24 h infusion 5-fluorouracil and folinic acid in patients with inoperable pancreatic cancer", *Anticancer Drugs*, 1999;10(8):699-704.

Offensperger et al., "In Vivo inhibition of duck hepatitis B virus replication and gene expression b phosphorothioate modified antisence oligodeoxynucleotides", *EMBO J.*, 12(3):1257-1262 (1993).

O'Keefe et al., "Mouse Plasmacytoid Cells: Long-lived Cells, Heterogeneous in Surface Phenotype and Function, that Differentiate Into $CD8^+$ Dendritic Cells Only after Microbial Stimulus," *J. Exp. Med.*, 2002;196:1307-1319.

Orenstein et al., "The Macrophage Origin of the HIV-Expressing Multinucleated Giant Cells in Hyperplastic Tonsils and Adenoids," *Ultrastruct. Pathol.*, 1999;23:79-91.

Orlando et al., "Gemcitabine in ovarian cancer", *Semin Oncol.* Jun. 2001;28(3 Suppl 10):62-69.

Orson et al., "Oligonucleotide inhibition of IL2Rα mRNA transcription by promoter region collinear riplex formation in lmphocytes", *Nucl. Acids Res.*, 19:3435-3441 (1991).

Ottaviani et al., "The invertebrate phagocytic immunocyte: clues to a common evolution of immune and neuroendocrine systems", *Immunol. Today*, 18(4):169-174 (1997).

Ozaki et al., "Induction of indoleamine 2,3-dioxygenase: A mechanism of the antitumor activity of interferon γ", *Proc. Natl. Acad. Sci. USA*, 85:1242-1246 (1988).

Pardoll, "Does the Immune System See Tumors as Foreign or Self?," *Ann. Rev. Immunol*, 2003;21:807-839.

Perry et al., "The Use of 3D Modelling Databases for Identifying Structure Activity Relationships", *OSAR: Quantitative Structure-Activity Relationships in Drug Design, Proceedings of the 7th European Symposium on OSAR* held in Interlaken, Switzerland, Sep. 5-9, 1988, Alan R. Liss, Inc.—New York, pp. 189-193 (1989).

Peterson et al., "Evaluation of Functionalized Tryptophan Derivatives and Related Compounds as Competitive Inhibitors of Indoleamine 2,3-Dioxygenase", *Med. Chem. Res.*, 3:531-544 (1994).

Pfefferkorn, "Interferon γ blocks the growth of *Toxoplasma gondii* in human fibroblasts by inducing the host cells to degrade tryptophan", *Proc. Natl. Acad. Sci. USA*, 81:908-912 (1984).

Postel et al., Evidence that a triplex-forming oligodeoxyibonucleotide binds to the c-myc promoter in heLa cells, thereby reduding c-myc mRNA levels, *Proc. Natl. Acad. Sci. USA*, 88:8227-8231 (1991).

Potter et al., "Enhancer-dependent expression of human κ immunoglobulin genes introduced into mouse pre-B lymphocytes by electroporation",*Proc. Natl. Acad. Sci. USA*, 81:7161-7165 (1984).

Potula et al., Inhibition of indoleamine 2,3-dioxygenase (IDO) enhances elimination of virus-infected macrophages in an animal model of HIV-1 encephalitis, *Immunobiology, Blood*, Oct. 1, 2005, 106(7):233822390.

Prasad et al., "Relationship between Thyroid Hormone Transport and Neutral Amino Acid Transport in JAR Human Choriocarcinoma Cells", *Endocrinology*, 134(2):574-581 (1994).

Probst et al., "Inducible Transgenic Mice Reveal Resting Dendritic Cells as Potent Inducers of CD8+ T Cell Tolerance," *Immunity*, 2003;18:713-720.

Quill, "Anergy as a Mechanism of Peripheral T Cell Tolerance", *J. Immunol*, 156(4):1325-1327 (1996).

Raynovich, "Late-Stage Cancer Vaccines Set to Launch, with Five Major Players, Therapeutic Vaccines Could Transform Medical Care," *GEN Biobusiness Wall Street Biobeat*. Mar. 1, 2007. genengnews.com. *Gen.Eng. & Biotech. News*.

Reddy et al., "A Monocyte Conditioned Medium Is More Effective Than Defined Cytokines in Mediating the Terminal Maturation of Human Dendritic Cells," *Blood*, 1997:90:3640-3646.

Renault et al., "Base Transitions Are the Most Frequent Genetic Changes at P53 in Gastric Cancer", *Cancer Research*, 53:2614-2617 (1993).

Report on the Rare Diseases Research Activities at the National Institutes of Health FY 2003. NSC No. 721782 (Group 2A, p. 13). 17 pages. Retrieved from the Internet on Jul. 29, 2004 at http://rarediseases.info.nih.gov/html/reports/fy2003/nci.html.

Restito et al., "Basic Aspects of Tumor Immunology," #346 Keystone Symposia 2003 Abstract Book. Abstract/Poster. Keystone, Colorado, Feb. 17-23, 2003. Meetings on Biomedical and Life Sciences that Encourage Scientific Information Exchange and Networking.

"Rheumatoid Arthritis," *Genetic Eng. & Biotech. News*, Mar. 1, 2007. Genengnews.com , (72) Translational Medicine.

Ridgway, "The First 1000 Dendritic Cell Vaccinees," *Cancer Invest*. 2003;21(6):873-886.

Romani et al., "Generation of mature dendritic cells from human blood: An improved method with special regard to clinical applicability," *J. Immunol. Methods*, 1996;196:137-151.

Ripka, "Computers picture the perfect drug", *New Scientist*, 54-57 (1988).

Rissoan et al., "Subtractive hybridization reveals the expression of immunoglobulinlike transcript 7, Eph-B1, granzyme B, and 3 novel transcripts in human plasmacytoid dendritic cells," *Blood*, 2002;100:3295-3303.

Rosenzwajg et al., Human Dendritic Cell Differentiation Pathway from CD34+ Hematopoietic Precursor Cells, *Blood*, 87(2):535-544 (1996).

Rosoff et al., "4,4'-Diisothiocyanatostilbene-2,2'-disulfonic Acid Inhibits CD3-T Cell Antigen Receptor-stimulated $Ca^{2+}$ Influx in Human T Lymphocytes", *J. Biol. Chem.*, 263(36):19535-19540 (1988).

Rotivinen et al., "Computer-Aided Drug Design", *Acta Pharmaceutica Fennica*, 97:159-166 (1988).

Rubin et al., Interferon Induces Tryptophanyl-tRNA Synthetase Expression in Human Fibroblasts, *The Journal of Biological Chemistry*, 266(36):24245-24248 (1991).

Saadi et al., "Immunology of Xenotransplantation" *Life Sciences*, 62(5):365-387 (1998).

Sallusto et al., "Efficient Presentation of Soluble Antigen by Cultured Human Dendritic Cells is Maintained by Granulocyte/Macrophage Colony-stimulating Factor Plus Interleukin 4 and Downregulated by Tumor Necrosis Factor α," *J. Exp. Med.*, 1994;179:1109-1118.

Sambrook et al., Molecular Cloning: A Laboratory Manual, Second Edition, Books 1-3, Cold Spring Harbor Laboratory Press, Cold Spring Harbor, New York, Title page and Table of Contents only, 29 pages (1989).

Sanchez del Pino et al., "Neutral Amino Acid Transport Characterization of Isolated Luminal and Abluminal Membranes of the Blood-Brain Barrier", *The Journal of Biological Chemistry*, 270(25):14913-14918 (1995).

Sardar et al., "Frontal cortex indoleamine-2,3-dioxygenase activity is increased in HIV-1-associated dementia", *Neurosci. Let.*, 187:9-12 (1995).

Sarin et al., "Inhibition of acquired immunodeficiency syndrome virus by oligodeoxynucleoside methylphosphonates", *Proc. Natl. Acad. Sci. USA*, 85:7448-7451 (1988).

Sarkhosh et al., "Immune cell proliferation is suppressed by the interferon-gamma-induced indoleamine 2,3-dioxygenase expression of fibroblasts populated in collagen gel (FPGG)," *J. Cell Biochem.* 2003, 1;90(1):206-217.

Schaller et al., "Identification of the Disulfide Bonds of the Human Complement Component C9 and Comparison with the Other Terminal Compoennts of the Membrane Attack Complex", *MPSA Short Communications*, pp. 472-473 (1996).

Schröder et al., "Suppression of the Modulatory Effects of the Antileukemic and Anti-Human Immunodeficiency Virus Compound Avarol on Gene Expression by Tryptophan", *Cancer Research*, 49(8):2069-2076 (1989).

Serreze et al., Defects in the Differentiation and Function of Antigen Presenting Cells in NOD/Lt Mice, *J. Immunol.*, 150(6):2534-2543 (1993).

Seymour et al., "Identification and Characterization of a Novel, High-Affinity Tryptophan-Selective Transport System in Human Macrophages", *Blood*, 90(10):448a, Abstract only (1997).

Shaw et al., "Modified deoxyoligonucleotides stable to exonuclease degradation in serum", *Nucleic Acids Res.*, 19(4):747-750 (1991).

Shortman et al., "Immunity or tolerance? That is the question for dendritic cells," *Nature Immunol*. 2001;2:988-989.

Shurin et al., "FLT3 Ligand Induces the Generation of Functionally Active Dendritic Cells in Mice," *Cell Immunol.* 1997;179:174-184.

Sidransky et al., "Effect of Tryptophan on Hepatoma and Host Liver of Rats. Influence After Treatment with Hypertonic Sodium Chloride and Carbon Tetrachloride", *Exp. Mol. Pathol.*, 35(1):124-136 (1981).

Sigalla et al. "Adenovirus-mediated gene transfer into isolated mouse adult pancreatic islets: normal beta-cell function despite induction of an anti-adenovirus immune response." *Hum Gene Ther* Sep. 1, 1997;8(13) 1625-1634.

Smith et al., "The host environment promotes the development of primary and metastatic squamous cell carcinomas that constitutively express proinflammatory cytokines IL-1α, IL-6, GM-CSF, and KC," *Clin. Exp. Metastasis*, 1998;16:655-664.

Smyth et al., "A Fresh look at tumor immunosurveillance and immunotherapy," *Nat. Immunol.*, 2001;2:293-299.

Sono et al., "Indoleamine 2,3-Dioxygenase. Equilibrium Studies of the Tryptophan Binding to the Ferric, Ferrous, and Co-Bound Enzymes", *J. Biol. Chem.*, 255(4):1339-1345 (1980).

Sotomayor et al., "Cross-presentation of tumor antigens by bone marrow-derived antigen-presenting cells is the dominant mechanism in the induction of T-cell tolerance during B-cell lymphoma progression," *Blood*, 2001;98,1070-1077.

Southan et al., Structural requirements of the competitive binding site of recombinant human indoleamine 2,3-dioxygenase, *Med. Chem. Res.*, 6:343-352 (1996).

Speiser et al., "Self Antigens expressed by solid tumors do not efficiently stimulate naive or activated T cells: implications for immunotherapy," *J. Exp. Med.*, 1997;186:645-653.

Sponass et al., "Induction of tolerance to self MHC class I molecules expressed under the control of milk protein or β-globin gene promoters," *Intl. Immun.*, vol. 6, No. 2, pp. 277-287.

Springer, "Traffic Signals for Lymphocyte Recirculation and Leukocyte Emigration: The Multistep Paradigm", *Cell*, 76:301-314 (1994).

Staveley-O'Carroll et al., "Induction of antigen-specific T cell anergy: an early event in the course of tumor progression," *Proc. Natl. Acad. Sci. USA*, 1998;95:1178-1183.

Steckel et al., "Indoleamine 2,3-Dioxygenase expression in patients with acute graft-;versus-host disease after allogeneic stem cell transplantation and in pregnant women: association with the induction of allogeneic immune tolerance?," 2003, *Scandinavian Journ. Of Immun.*, 57, pp. 185-191.
Steinbrink et al., "Induction of Tolerance by IL-10-Treated Dendritic Cells," *J. Immunol.*, 1997;159:4772-4780.
Steinman, "Escape from "Horror Autotoxicus": Pathogenesis and Treatment of Autoimmune Disease", *Cell*, 80:7-10 (1995).
Steinman et al., "The Endocytic Activity of Dendritic Cells," *Exp. Med.* 1995;182:283-288.
Steinman et al., "Avoiding horror autotoxicus: the importance of dendritic cells in peripheral T cell tolerance," *Proc. Natl. Acad. Sci. USA* 2002;99:351-358.
Sternberg et al., "Development of a Scleroderma-Like Illness During Therapy with L5-Hydroxytryptophan and Carbidopa",*N. Engl. J. Med.*, 303(14):782-787 (1980).
Summers et al., "Phenotypic Characterization of Five Dendritic Cell Subsets in Human Tonsils," *Am. J. Pathol.* 2001;159:285-295.
Sutmuller et al., "Synergism of Cytotoxic T Lymphocyte-associated Antigen 4 Blockade and Depletion of $CD25^+$ Regulatory T Cells in Antitumor Therapy Reveals Alternative Pathways for Suppression of Autoreactive Cytotoxic T Lymphocyte Responses," *J. Exp. Med.*, 2001;194:823-832.
Suzuki, "Abalone Myoglobins Evolved from Indoleamine Dioxygenase: The cDNA-Derived Amino Acid Sequence of Myoglobin from *Nordotis madaka*", *Journal of Protein Chemistry*, 14(1):9-13 (1994).
Suzuki et al., "Convergent evolution. The gene structure of *Sulculus* 41 kDa myoglobin is homologous with that of human indoleamine dioxygenase", *Blood*, 87:4520-4530 (1996).
Suzuki et al., "Convergent evolution. The gene structure of Sulculus 41 kDa myoglobin is homologous with that of human indoleamine dioxygenase," *Biochem. Biophys. Acta*, 1308:41-48 (1996).
Swanson et al., "$CD11c^+$ Cells Modulate Pulmonary Immune Responses by Production of Indoleamine 2,3-Dioxygenase," 2004, *Am. Journ. Of Respiratory Cell and Molecular Biology*, vol. 30, pp. 311-318.
Szabolcs et al., "Dendritic Cells and Macrophages Can Mature Independently From a Human Bone Marrow-Derived, Post-Colony-Forming Unit Intermediate", *Blood*, 87(11):4520-4530 (1996).
Szostak, "In vitro genetics", *TIBS*, 17(3):89-93 (1992).
Tafuri et al., "T Cell Awareness of Paternal Alloantigens During Pregnancy", *Science*, 270:630-633 (1995).
Takikawa et al., "Mechanism of Interferon-γ Action. Characterization of Indoleamine 2,3-Dioxygenase in Cultured Human Cells Induced by Interferon-γ and Evaluation of the Enzyme-Mediated Tryptophan Degradation in its Anticellular Activity", *The Journal of Biological Chemistry*, 263(4):2041-2048 (1988).
Takikawa et al., (1990) "IFN-γ Is the Inducer of Indoleamine 2,3-Dioxygenase in Allografted Tumor Cells Undergoing Rejection," *J. Immunol.*, vol. 145(4), 1246-1250.
Takikawa et al., "Induction of Indoleamine 2,3-Dioxygenase in Tumor Cells Implanted Into Allogeneic Mouse: Interferon-γ is the Inducer", *Kynurenine and Serotonin Pathways*, pp. 437-444, Plenum Press: New York (1991).
Tarazona et al., "Effects of different antigenic microenvironments on the course of $CD8^+$ T cell responses in vivo", *Intl. Immunol.*, 8(3):351-358 (1996).
Taylor et al., "Relationship between interferon-gamma, indoleamine 2,3-dioxygenase, and tryptophan catabolism", *FASEB J.*, 5:2516-2522 (1991).
Terness et al., "Inhibition of allogeneic T cell proliferation by Indoleamine 2,3-Dioxygenase-expressing dendritic cells: mediation of suppression by tryptophan metabolites," 2002, *J. Exp. Med.* vol. 196, No. 4, pp. 447-457.
Thomas et al., "IFN-gamma-mediated antimicrobial response. Indoleamine 2,3-diioxygenase-deficient mutant host cells no longer inhibit intracellular Chlamydia spp. Or Toxoplasma grouth", *J. Immunol.*, 150:5529-5534 (1993).
Thomas et al., "Nitric Oxide Inhibits Indoleamine 2,3-Dioxygense Activity in Interferon-γ Primed Mononuclear Phagocytes", *J. Biol. Chem.*, 269(20):14457-14464 (1994).
Thomas et al., "Dendritic Cells: Origin and Differentiation", *Stem Cells*, 14:196-206 (1996).

Thomas et al., "Are dendritic cells the key to liver transplant tolerance?", *Immunology Today*, 6 pgs. (1999).
Thomas et al., "Antioxidants Inhibit Indoleamine 2,3-Dioxygenase in IFN-γ-Activated Human Macrophages: Posttranslational Regulation by Pyrrolidine Dithiocarbamate," *J. Immunol.*, 2001;166:6332-6340.
Torre et al., "Immunological Aspects of Nitric Oxide in HIV-1 Infection", *Medical Hypotheses*, 47:405-407 (1996).
Trinchieri et al., "Immunoregulation by interleukin-12", *Journal of Leukocyte Biology*, 59:505-511 (1996).
Unanue et al., The Basis for the Immunoregulatory Role of Macrophages and Other Accessory Cells, *Science*, 236:551-557 (1987).
Uyttenhove et al., "Evidence for a tumoral immune resistance mechanism based on tryptophan degradation by Indoleamine 2,3-dioxygenase", *Nature Medicine* 2003;9(10):1269-1274. Epub Sep. 21, 2003.
van Elsas et al., "Combination Immunotherapy of B16 Melanoma Using Anti-Cytotoxic T Luymphocyte-associated Antigen 4 (CTLA-4) and Granulocyte/Macrophage Colony-Stimulating Factor (GM-CSF)-producing Vaccines Induces Rejection of Subcutaneous and Metastic Tumors Accompanied by Autoimmune Depigmentation," *J. Exp. Med.* 1999;190(3):355-366.
Venkateshan et al., "Immunocytochemical localization of the endogenous neuroexcitotoxin quinolinate in human peripheral blood monocytes/macrophages and the effect of human T-cell lymphotropic virus type I infection",*Proc. Natl. Acad. Sci. USA*, 93:1636-1641 (1996).
Vicari et al., "Reversal of Tumor-induced Dendritic Cell Paralysis by CpG Immunostimulatory Oligonucleotide and Anti-Interleukin 10 Receptor Antibody," *J. Exp. Med.*, 2002;196:541-548.
Vogelgesang et al., "Quinolinic Acid in Patients with Systemic Lupus Erythematosus and Neuropsychiatric Manifestations",*J. Rheumatol*, 23(5):850-855 (1996).
Weber, et al. "Adenoviral transfection of isolated pancreatic islets: a study of programmed cell death (apoptosis) and islet function." *J Surg Res* Apr. 1997;69(1):23-32.
Weiss et al., "Linkage of cell-mediated immunity to iron metabolism", *Immunology Today*, 16(10):495-500 (1995).
Werner et al., Human Macrophages Degrade Tryptophan Upon Induction by Interferon-Gamma, *Life Sciences*, 41(3):273-280 (1987).
Wick et al., "Antigenic Cancer Cells Grow Progressively in Immune Hosts without Evidence for T Cell Exhaustion or Systemic Anergy," *J. Exp. Med.*, 1997;186:229-238.
Wickstrom et al., "Human promyelocytic leukemia HL-60 cell proliferation and *c-myc* protein expression are inhibited by an antisense pentadecadeoxynucleotide targeted against *c-myc* mRNA", *Proc. Natl. Acad. Sci. USA*, 85:1028-1032 (1988).
Willenborg et al., IFN-γ Plays a Critical Down-Regulatory Role in the Induction and Effector Phase of Myelin Oligodendrocyte Glycoprotein-Induced Autoimmune Encephalomyelitis, *J. Immunol*, 157:3223-3227 (1996).
Yang et al., "Cutting Edge: Immature Dendritic Cells Generated from Monocytes in the Presence of TFG-β1 Express Functional C-C Chemokine Receptor 6," *J. Immunol.*, 1999;163:1737-1741.
Yang et al., "Cancer-associated immunodeficiency and dendritic cell abnormalities mediated by the prostaglandin EP2 receptor," *J. Clin. Invest.*, 2003;111:727-735.
Young et al., "Triple helix formation inhibits transcription elongation in vitro", *Proc. Natl. Acad. Sci. USA*, 88:10023-10026 (1991).
Yu et al., "Moleclar mechanisms underlying IFN-γ-mediated tumor growth inhibition induced during tumor immunotherapy with rIL-12", *Int. Immunol*, 8(6):855-865 (1996).
Yu et al., "Combination of γ-Irradiation and Dendritic Cell Administration Induces a Potent Antitumor Response in Tumor-Bearing Mice: Approach to Treatment of Advanced Stage Cancer," *Int. J. Cancer*, 2001;94:825-833.
Yu et al., "Cancer vaccines: progress reveals new complexities," *Journ. of Clinical Investigation* 2002;110:289-294.
Zamecnik et al., "Inhibition of Rous sarcoma virus replication and cell transformation by a specific oligodeoxynucleotide", *Proc. Natl. Acad. Sci. USA*, 75:280-284 (1978).
Zamecnik et al., Inhibition of replication and expression of human T-cell lymphotropic virus type III in cultured cells by exogenous systhenic oligonucleotides complementary to viral RNA, *Proc. Natl. Acad. Sci. USA*, 83:4143-4146 (1986).

Zhou et al., "Expanded cohorts of maternal CD8 + T-cells specific for paternal MHC class I accumlate during pregnancy", *J. Reprod. Immunol.*, 40:47-62 (1998).

Zhou et al., "Evidence for a Close Link between the Thyroid Hormone Transport System and the Aromatic Amino Acid Transport System T in Erythrocytes", *J. Biol. Chem.*, 265(28):17000-17004 (1990).

Zhu et al., "Systemic Gene Expression After Intravenous DNA Delivery into Adult Mice", *Science*, 261:209-211 (1993).

Zimmer et al., "Production of chimaeric mice containing embryonic stem (ES) cells carrying a homoeobox Hox 1.1 allele mutated by homologous recombination", *Nature*, 338:150-153 (1989).

Pinedo, et al., "Biological Concepts of Prolonged Neoadjuvant Treatment plus GM-CSF in Locally Advanced Tumors," *The Oncologist*. 2000, 5:497-500.

Tsung, et al., "Immune Response Against Large Tumors Eradicated by Treatment with Cyclophosphamide and IL-12," *The Journal of Immunology*. 1998. pp. 1370-1377.

Boasso et al., "Combined Effect of Antiretroviral Therapy and Blockade of IDO in SIV-Infected Rhesus Macaques," 2009. *J. Immunol.*, 182:4313-4320.

Kuhn et al. "Adsorption Chromatography on Cellulose. IV. Separation of D- and L-Tryptophan and D- and L-Methyl-Tryptophan on Cellulose with Aqueous Solvents". 1989. *Journ. Of Chromatography*, 469:253-260.

U.S. Appl. No. 12/548,657, filed Aug. 27, 2009, Munn et al.

U.S. Appl. No. 12/526,909, filed Nov. 12, 2009, Sharma et al.

Fallarino et al., "Murine Plasmacytoid Dendritic Cells Initiate the Immunosuppressive Pathway of Tryptophan Catabolism in Response to CD200 Receptor Engagement," Journ. Of Immunology. 2004. 173(6):3748-3754.

Heikenwalder et al., "Lymphoid follicle destruction and immunosuppression after repeated CpG oligodeoxynucleotide administration," *Nature Medicine*, 2004. 10(2):187-192.

Muller et al., "Inhibition of indoleamine 2,3-dioxygenase, an immunoregulatory target of the cancer suppression gene Bin1, potentiates cancer chemotheraphy," *Nature Medicine*, 2005. 11(3)312-319.

* cited by examiner

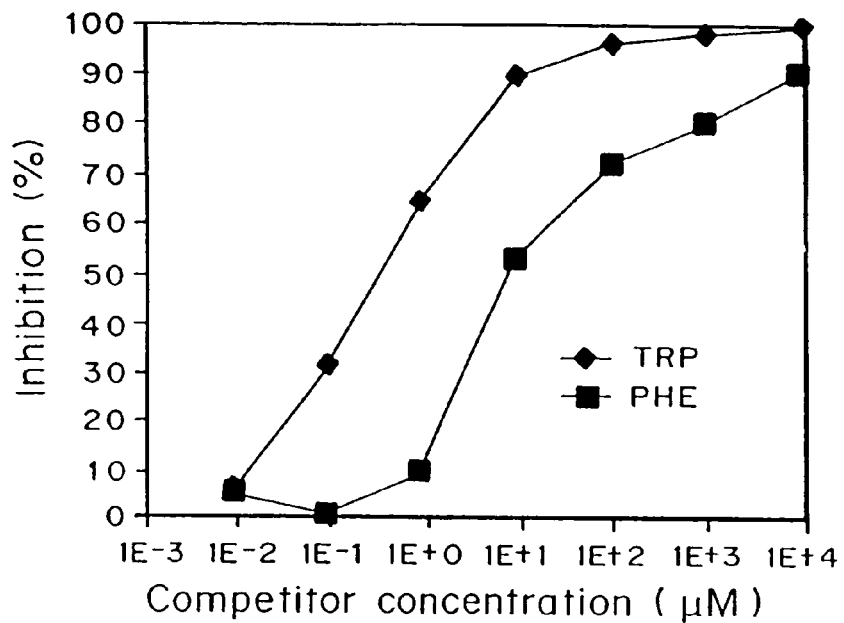
FIG. 9
FIG. 10
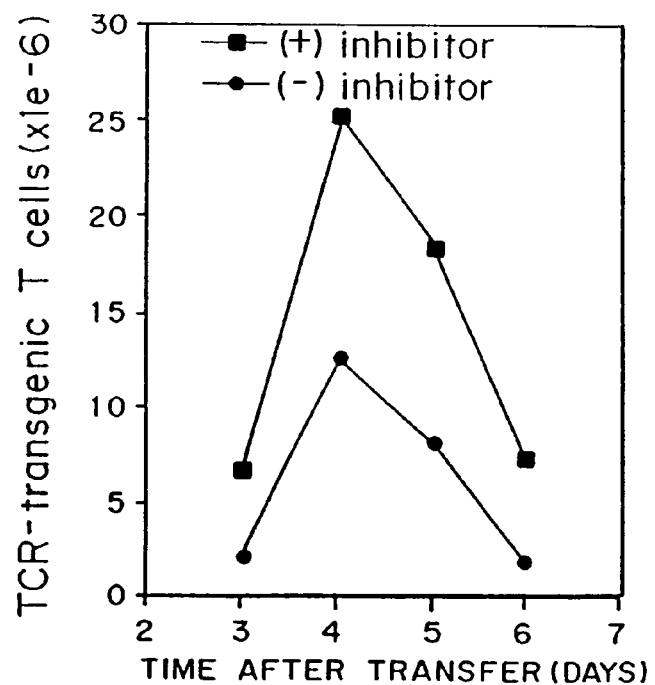
FIG. 11

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gtacatcacc atggcgtatg                    20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
gctttcgtca agtcttcatt g                  21

REGULATION OF T CELL-MEDIATED IMMUNITY BY TRYPTOPHAN

This application is a divisional application of U.S. application Ser. No. 10/112,362, filed on Mar. 28, 2002, now U.S. Pat. No. 7,160,539, issued Jan. 9, 2007; which is a divisional of U.S. application Ser. No. 09/206,274, filed on Dec. 4, 1998, now U.S. Pat. No. 6,451,840, issued Sep. 17, 2002; which claims priority to U.S. Ser. No. 60/067,610 filed Dec. 5, 1997; U.S. Ser. No. 60/080,384 filed Apr. 1, 1998; and U.S. Ser. No. 60/080,380 filed Apr. 1, 1998. U.S. application Ser. No. 09/727,055, filed Nov. 30, 2000, now U.S. Pat. 6,482,416, issued Nov. 19, 2002 is a divisional of U.S. application Ser. No. 09/206,274 filed on Dec. 4, 1998, now U.S. Pat. No. 6,451,840 issued Sep. 17 2002. All of these as applications are incorporated by reference.

The present invention was made with government support under Grant No. K08 HL 03395, awarded by the National Institutes of Health. The Government has certain rights in this invention.

The present invention is generally in the area of regulation of T cell activation using modulators of the enzyme indoleamine 2,3-dioxygenase (IDO) which is used by immunosuppressive antigen-presenting cells such as tissue macrophages and placental trophoblasts to prevent T cells from activating in response to antigens presented by these cells. Modulation of the enzyme activity can therefore be used to affect pregnancy, infection by certain viruses such as HIV, and inflammation. More specifically, the present invention includes altering maternal tolerance of pregnancy using modulators of the enzyme indoleamine 2,3-dioxygenase (IDO) which is used by immunosuppressive antigen-presenting cells such as tissue macrophages and placental trophoblasts to prevent T cells from activating in response to antigens presented by these cells.

BACKGROUND OF THE INVENTION

Traditionally, the "professional" antigen-presenting cells (APCs) of the myeloid lineage, dendritic cells and macrophages, have been viewed primarily as accessory cells, functioning simply to assist T cell activation. Recently, however, it has become clear that myeloid-lineage APCs exert a profound influence on T cells, regulating both the nature of the response (humoral versus cellular immunity) and, in some cases, even whether a response occurs at all (activation versus anergy). This has been the subject of recent reviews by Fearon and Locksley (*Science* 1996;272:50-54) and Trinchieri and Gerosa (*J. Leukocyte Biol.* 1996;59:505-511). Currently, the biology of myeloid-lineage APCs is not well understood. Dendritic cells and macrophages appear to derive from a common progenitor in the myelomonocytic lineage (Szabolcs, et al. *Blood* 1996;87:4520-4530), but their markedly different functional characteristics are determined during a complex process of hematopoietic differentiation, which continues well after their exit from the bone marrow (Thomas, et al. *Stem Cells* 1996;14:196-206). Hematopoietic differentiation has traditionally fallen outside the purview of classical immunology.

Macrophages enter the tissues at the immature stage of circulating monocytes. Using in vitro models, it has been shown that the cytokine milieu which they encounter at this early stage determines the phenotype which they will subsequently adopt. Under the influence of certain cytokines (in humans, usually GM-CFS plus IL-4 or TNF), monocytes differentiate in vitro into cells which closely resemble dendritic cells (Mackensen, et al. *Blood* 1995; 86:2699-2707; Rosenzwajg, et al., *Blood* 1996; 87:535-544). In the presence of inflammatory cytokines they differentiate into macrophages activated for antigen presentation and host defense (Munn et al., *Cancer Res.* 1993; 53:2603-2613; Morahan, et al. In: Heppner G H, Fulton A M, eds. Macrophages and Cancer, Boca Raton, Fla.; CRC Press, 1988:1-25). In the absence of inflammatory cytokines, monocytes differentiate under the influence of their lineage-specific growth factor, MCSF, into a type of macrophage which inhibits, rather than supports, T cell activation (Munn, et al. *J. Immunol.* 1996; 156:523-532).

The adaptive immune system must tailor the T cell repertoire so as not to respond to self antigens. The classical model (reviewed by Nossal in *Cell* 1994;76:229-239) holds that autoreactive T cell clones are deleted in the thymus via the process of negative selection (encounter with antigen at the immature thymocyte stage triggers apoptosis, resulting in clonal deletion). Although the thymus undoubtedly provides a major site of negative selection, there are two difficulties with this model. First, it would seem unlikely that every developing T cell could be exposed to every self protein during its relatively brief transit through the thymus. Second, autoreactive T cells are empirically found in the peripheral blood of normal, healthy hosts (Steinman *Cell* 1995;80:7-10). This suggests that there must exist some additional means of tailoring the T cell repertoire after the T cells have left the thymus, a process now designated peripheral tolerance. Multiple mechanisms have been proposed to contribute to peripheral tolerance (for recent reviews see Steinman L. *Cell* 1995; 80:7-10; Mondino, et al. *Proc. Natl. Acad. Sci USA* 1996;93: 2245-2252; and Quill H. *J. Immunol.* 1996;156:1325-1327).

Most recent studies support a model in which dendritic cells are the primary physiologic route of antigen presentation to T cells (Thomas et al. 1996). Under normal circumstances, this process is felt to occur only in lymph nodes. Given this exclusive role for dendritic cells in initiating immune responses, tissue macrophages represent a paradox. They are professional APCs, but they are also professional scavengers of all manner of damaged cells and proteins, and hence take up a huge array of self antigens. Moreover, unlike dendritic cells, many of them constitutively express MHC and costimulatory ligands (Azuma, et al. *Nature* 1993; 366:76-79) and function as APCs in vitro (Unanue, et al. *Science* 1987; 236:551-557), implying they are constantly prepared to present antigen.

It is not known how they avoid provoking autoimmune responses. One possibility is that T cells never encounter tissue macrophages. This may indeed be the case for naive T cells, since they are not thought to circulate through tissues (Springer, et al. *Cell* 1994;76:301-314). However, at times of injury and inflammation, many self antigens unavoidably enter the normal antigen-presentation pathway along with legitimate foreign antigens (either because the dendritic cell has no way to discriminate between the two, or due to influx of debris from damaged tissues into the draining lymph nodes (Steinman 995)).

Certain pathological conditions, such as AIDs (caused by the human immunodeficiency virus, HIV) and latent cytomegaloviral (CMV) infections, are extremely difficult to treat since the macrophages act as reservoirs for the viruses. Even though the cells are infected with virus, they are not recognized as foreign. It is not known why these cells are protected from the host's immune system.

It is therefore an object of the present invention to identify mechanisms by which tissue macrophages regulate T cell activation in order to modulate autoimmune responses to the self-derived antigens which they present, especially in the context of infections with facultative intracellular pathogens, such as HIV and CMV.

It has long been a mystery why a pregnant individual does not reject her fetus as foreign. Many theories have been proposed, and various mechanisms suggested. Being able to understand and control this phenomena would be of benefit both for the development of contraceptives or aborticides, as well as in treatment of some women who are unable to carry a fetus full term. Medawar, 1953, *Symp. Soc. Exp. Biol.* 7, 320-338, pointed out 45 years ago that the mammalian conceptus ought to survive gestation because it carries and expresses paternally-inherited polymorphic genes that provide maternal immune responses when expressed by other tissues. The paradox presented by survival of fetal allografts has not yet been explained in mechanistic terms despite much research on the immunology of mammalian reproduction.

Three factors that might explain the immunological paradox of fetal survival are: (1) anatomic separation of mother and fetus, (2) antigenic immaturity of the fetus and (3) immunologic "inertness" (tolerance) of the mother (Medawar 1953). Recently, attention has focused on the third possibility based on evidence that the entire maternal T cell repertoire is transiently tolerized to paternal MHC class I alloantigens during pregnancy (Tafuri, et al., 1995, Science 270, 630-633). However, it is not clear how transient tolerance is imposed and maintained in the peripheral T cell repertoire during pregnancy.

It is therefor an object of the present invention to identify mechanisms by which rejection of the fetus by its mother are prevented.

It is a further object of the present invention to provide reagents and methods for use thereof for terminating or maintaining pregnancies.

SUMMARY OF THE INVENTION

A mechanism of macrophage-induced T cell suppression is the selective elimination of tryptophan and/or increase in one or more tryptophan metabolites within the local macrophage microenvironment via simultaneous induction of the enzyme indoleamine 2,3-dioxygenase (IDO) and a tryptophan-selective transport system. Studies demonstrate that expression of IDO can serve as a marker of suppression of T cell activation, and may play a significant role in allogeneic pregnancy and therefore other types of transplantation, and that inhibitors of IDO can be used to activate T cells and therefore enhance T cell activation when the T cells are suppressed by malignancy or a virus such as HIV. Inhibiting tryptophan degradation (and thereby increasing tryptophan concentration while decreasing tryptophan metabolite concentration), or supplementing tryptophan concentration, can therefore be used in addition to, or in place of, inhibitors of IDO. Similarly, increasing tryptophan degradation (thereby, decreasing tryptophan concentration and increasing tryptophan metabolite concentration), for example, by increasing IDO concentration or IDO activity, can suppress T cells. Although described particularly with reference to IDO regulation, one can instead manipulate local tryptophan concentrations, and/or modulate the activity of the high affinity tryptophan transporter, and/or administer other tryptophan degrading enzymes. Regulation can be further manipulated using cytokines such as macrophage colony stimulating factor, interferon gamma, alone or in combination with antigen or other cytokines.

Studies demonstrate that expression of IDO can serve as a marker of suppression of T cell activation, and plays a significant role in allogeneic pregnancy. Inhibitors of IDO can be used to activate T cells and thereby induce rejection of a fetus. Studies show that administration of an inhibitor of IDO, 1-methyl-tryptophan, induces specific and uniform rejection of allogeneic conceptus. Embryo loss is preceded by extensive inflammation, the appearance of monocuclear and neutrophil infiltrates, and degeneration of decidual tissues. Rejection is T cell driven since a single paternally-inherited fetal MHC class I alloantigen provokes embryo loss, and rejection does not occur if maternal lymphocytes are absent when IDO activity is inhibited or the mother does not have functional T cells.

Administration of an inhibitor of IDO, 1-methyltryptophan, can cause rejection of foreign tissue without toxicity. These studies provide a mechanism whereby facultative intracellular pathogens are able to avoid destruction by the host's T cells, even when the macrophages express viral antigens on their surfaces. Inhibition of IDO should cause the host to attack and kill the infected macrophages. In a preferred embodiment for treatment of HIV, the viral load is decreased using standard HIV therapy, usually over a period of three to six months. This is then followed by treatment with an inhibitor of IDO such as 1-methyltryptophan at a dose equivalent to 1 g/kg, for a period of between one day and a few weeks. For treatment of CMV infections, especially before cancer chemotherapy or bone marrow transplant, the patient is treated with an inhibitor of IDO for a period effective for the patient's own T cells to attack and kill any infected macrophages. Malignancies are treated with an IDO inhibitor until the tumor(s) is necrotic or the cancer is in remission.

BRIEF DESCRIPTION OF THE DRAWINGS

In FIG. 4B, macrophages were seeded at both low density ($5 \times 10^4$/well) and high density ($2 \times 10^5$/well). In both parcels, all differences discussed as significant were $p < 0.01$ by ANOVA and Tukey's.

FIG. 7A shows uptake of [$^3$H] tryptophan (200 nM) was measured for the times indicated, then cells were washed onto glass fiber filters and assayed by liquid scintillation counting. The graph compares fresh monocytes, MCSF-derived macrophages (day 7), and MCSF-derived macrophages activated for the preceding 24 hrs with IFNγ. All assays were performed in the presence of 140 mM NaCl. FIG. 7B shows sodium-dependent and sodium-independent (140 mM choline chloride) uptake for T cells activated for 72 hrs with anti-CD3, then assayed as in FIG. 7A. A logarithmic scale is used to permit comparison.

FIG. 9 is a graph of percent inhibition versus concentration of competitor (tryptophan or phenylalanine) showing that the tryptophan transport system in MCSF-derived macrophages displays a preferential affinity for tryptophan. Macrophages were cultured for 7 days in MCSF and activated during the last 24 hrs with IFNγ. Uptake of [$^3$H]tryptophan (400 nM) was then assayed in the presence of various concentrations of unlabeled tryptophan or phenylalanine.

FIG. 10 are HPLC analyses showing elimination of autoreactive T cells in vivo is accompanied by tryptophan degradation. Antigen-transgenic mice received autoreactive T cells by adoptive transfer, and then were assayed for the tryptophan breakdown product kynurinine at a time when the T cells were being actively eliminated (day 3). Trace 1 shows HPLC analysis for kynurinine in control serum prior to adoptive transfer. Trace 3 shows control serum spiked with authentic kynurinine (10 µM). Trace 2 shows serum from mice on day 3 after adoptive transfer of T cells. The asterisk indicates the kynurinine peak.

FIG. 11 is a graph of autoreactive TcR-transgenic T cells ($1 \times 10^7$) over time (days) after adoptive transfer of cells with and without inhibitor.

DETAILED DESCRIPTION OF THE INVENTION

Figure 1:
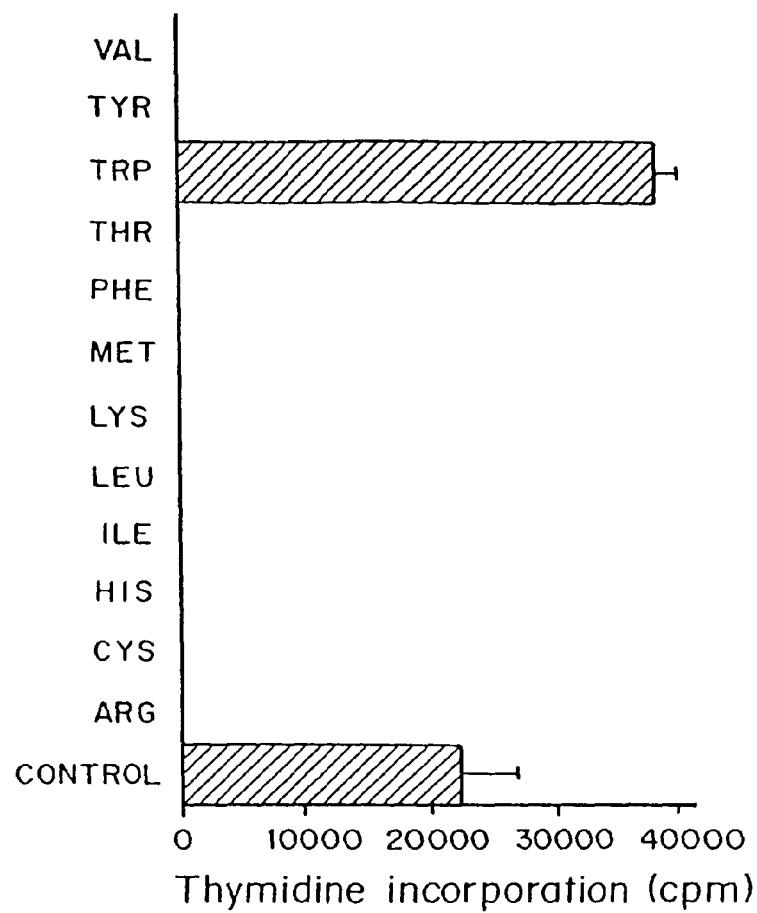
FIG. 1 is a graph of thymidine incorporation (cpm) by T cells in the presence of supplemental amino acids. Co-culture conditioned medium is selectively depleted of tryptophan. Human monocytes were allowed to differentiate into macrophages then co-cultured with mitogen-activated T cells (anti-CD3). Fresh PBMC were then suspended in this medium and activated with additional anti-CD3. Replicate cultures were supplemented with individual amino acids to the concentrations normally found in RPMI-1640. Control cultures received fresh medium. Proliferation was measured by 4 hr thymidine incorporation after 72 hrs. Error bars show SD.

Roles of IDO and Tryptophan in T Cell Activation

As monocytes differentiate into macrophages they can adopt markedly different phenotypes, depending on the cytokine milieu. Macrophages may present antigens in an immunosuppressive, rather than immunostimulatory fashion. Most phenotypes support T cell activation, but one, produced by exclusive exposure to the cytokine macrophage colony-stimulating factor (MCSF), suppresses T cell activation. It is proposed that macrophages discriminate which antigens are "self" based on the presence or absence of inflammation during terminal macrophage differentiation. Inflammatory cytokines such as IFNγ (Munn, et al. 1993; Munn, et al. 1996), IFNα, and IL-4 act dominantly over MCSF to prevent the development of the inhibitory macrophage phenotype. Thus, immunosuppressive macrophages should develop only if they differentiated in nonnal, uninflamed tissues. In such tissues, the only antigens encountered should be self-derived, and hence responding T cells would be presumptively autoreactive. This is conceptually related to proposed models of self/non-self discrimination such as the model described by Janeway *Immunol. Today* 1992; 13:11-16, in which antigens in normal tissues are considered self, and only in settings of inflammation or infection are T cells allowed to activate. This model has been subsequently reviewed by Ibrahim et al. in *Immunol. Today* 1995; 16:181-186.

The data and proposed mechanisms described herein complement these models by suggesting a specific mechanism by which antigens could be presented in noimal tissues in an immunosuppressive fashion. The mechanism of this suppression is via induction of the enzyme indoleamine 2,3-dioxygenase (IDO), which selectively degrades the essential amino acid tryptophan. In non-hepatic tissues, the enzyme responsible for the initial rate-limiting step in tryptophan degradation along the kynurinine pathway is indoleamine-2, 3-dioxygenase-(IDO) (Taylor, et al. *FASEB J.* 1991; 5:2516-2522). IDO is a subject of active current interest in the context of infectious disease (Pfefferkorn *Proc. Natl. Acad Sci. USA* 1984; 81:908-912; Gupta et al. *Infect. Immun.* 1994; 62:2277-2284; Musso et al.; *Blood* 1994; 83:1408-1411; Koide et al. *Infect. Immun.* 1994; 62:948-955; Daubener *Immunol.* 1995; 86:79-84; Daubener, et al., *Eur. J. Immunol.* 1996; 26:487-492; Carlin, et al. *J.Leuk Biol.* 1989; 45:29-34; Nagineni et al. *Infect. Immun.* 1996; 64:4188-4196), where it is postulated to reduce the intracellular concentration of tryptophan to the point that facultative intracellular pathogens are unable to replicate (tryptophan is an essential amino acid for all eukaryotic parasites, and for certain simple prokaryotes). Cell lines which have mutations in the IDO gene are unable to control the replication of organisms such as toxoplasma and chlamydia (Thomas et al. *J. Immunol.* 1993; 150:5529-5534). Conversely, pathogen-sensitive cell lines transfected with IDO acquire the ability to inhibit proliferation of these organisms (Gupta et al. *Infect. Immun.* 1994; 62:2277-2284). IDO may be particularly critical in defense against CNS and ocular toxoplasmosis, since glial and retinal cells show a direct correlation between IDO activity and control of toxoplasma (Daubener et al. *Eur. J. Immunol.* 1996; 26:487-492; Nagineni et al. *Infect. Immun.* 1996; 64:4188-4196). IDO may also contribute to the pathophysiology of central nervous system infection, autoimmune inflammation, and AIDS dementia, via both local tryptophan starvation and by generation of neurotoxic tryptophan metabolites such as quinolinate (Venkateshan et al. *Proc. Natl. Acad. Sci. USA* 1996; 93:1636-1641; Vogelgesang et al., *J. Rheumatol.* 1996; 23:850-855; *Sardar Neurosci. Let.* 1995; 187:9-12; Alberati-Giani et al. *J. Neurochem.* 1996; 66:996-1004).

IDO is induced by several inflammatory mediators, including interferons and LPS, as well as by viral infection (probably indirectly via interferons). The most potent inducer of IDO is IFN, due to two interferon-stimulated response elements (ISREs) in the IDO promoter (Konan et al. *J. Biol.*

*Chem.* 1996; 271:19140-19145; Chon et al. *J. Biol. Chem.* 1996; 271:17247-17252). In addition to its effect on intracellular organisms, IDO appears to mediate at least part of the antiproliferative effect of IFNγ on replicating host cells, such as virally infected cells and tumor cells (Aune, et al., 1989 *J. Clin. Invest.* 84, 863-875). Mutant cell lines selected for their ability to grow in the presence of IFNg were found to have acquired mutations in the IDO gene or its promoter (Feng et al. *Proc. Natl. Acad Sci USA* 1989; 86:7144-7148). Allogeneic tumor cells being rejected by the host immune system in vivo upregulate IDO, and this effect is mediated by IFNg (Takikawa, et al. In: Schwarcz R, ed. Kynurenine and Serotonin Pathways, New York: Plenum Press, 1991; 437-444; Yu, et al., *Intl. Immunol.* 1996; 8:855-865), although it is not known whether IDO plays a causal role in tumor rejection. Thus, IDO can inhibit proliferation of both intracellular pathogens and host cells.

The prior art in the field has viewed IDO solely as a means to reduce the concentration of tryptophan within the IDO-expressing cell (Taylor and Feng, 1991 *FASEB J.* 5:2516-2522). There has been no speculation that IDO could function to suppress proliferation of neighboring cells, and specifically no suggestion that it could be used to suppress T cell activation. Based on the in vitro studies described herein, the hypothesis was formulated that cells expressing IDO would be able to suppress T cell activation in vivo. From this hypothesis the testable prediction was formulated that inhibition of IDO enzyme activity with compounds such as 1-methyl-tryptophan would allow enhanced T activation in vivo. Review of the existing literature suggested that IDO activity was likely to be present in macrophage-like and dendritic-like cells in organs of the immune system (Moffett, et al., 1994 *Cell Tissue Res.* 278:461-469). Therefore, to test the hypothesis that IDO-expressing cells in the immune system suppressed autoreactive T cells in vivo, adoptive transfer studies were performed in which T cells which were transgenic for a defined T cell receptor were injected into recipient mice made transgenic for the cognate target antigen. This model of autoimmune T cell activation has been previously described by Tarazona, et al., 1996 *Int. Immunol.* 8:351-358. As shown in FIG. 10, the injection of autoreactive T cells resulted in induction of IDO (measured as elevated kynurenine in serum). When IDO activity was inhibited in recipient animals by administration of 1-methyl-tryptophan, the activation of the autoreactive T cells was markedly enhanced (2- to 3-fold over control, as shown by FIG. 11). These data thus supported the hypothesis that there existed a population of IDO-expressing cells which suppressed autoreactive T cells in vitro.

The in vitro data presented herein were derived using human monocyte-derived macrophages. For convenience, the term "macrophage" is therefore used to describe any IDO-expressing cell which suppresses T cell activation. However, in vivo this cell could be a macrophage, dendritic cell, or other cell type with expresses IDO and suppresses T cells.

As determined in the studies described herein, macrophages are primed during differentiation in the presence of MCSF to undergo a massive induction of IDO activity in response to a synergistic combination of signals displayed during early T cell activation (IFNγ plus CD40 ligand). In addition, these macrophages markedly increase their rate of tryptophan uptake, via induction of a previously unidentified high-affinity transport pathway. Macrophages which have differentiated under the influence of macrophage colony-stimulating factor (MCSF) inhibit attempted T cell activation via super-induction of the antimicrobial host-defense enzyme indoleamine 2,3-dioxygenase, which selectively degrades the essential amino acid tryptophan. Simultaneously, these macrophages also markedly increase tryptophan uptake via induction of a novel high-affinity transport pathway. The combination of these two mechanisms allows macrophages of this phenotype to effectively deplete tryptophan from the local microenvironment, thus preventing T cell activation.

Nutrient depletion is an evolutionarily ancient strategy, and as the utility of L-asparaginase against leukemia attests it remains an effective one. The best studied example of this type of mechanism in humans is chelation of iron, an essential micronutrient for all dividing cells. Microbes employ this strategy against each other (deferoxamine is an example), and so do macrophages via the secretion of the iron-chelating protein lactoferrin (Baynes *Adv. Exp. Med. Biol.* 1994;357: 133-141). Macrophages use iron depletion as a cytostatic mechanism against tumor cells and other dividing cells (reviewed in Weiss, et al. *Immunology Today* 1995;16:495-500), and iron is rapidly sequestered from serum and tissues by macrophages in response to infection and inflammation. Another example of regulation by nutrient depletion is the ability of macrophages to alter the intracellular thiol pool in T cells via degradation of cysteine, resulting in thiol-mediated redox regulation of T cell activation (Gmunder, et al. *Cell. Immunol.* 1990; 129:32-46; Iwata, et al., *J. Immunol.* 1994; 152:5633-5642). Thus, tryptophan degradation is not a unique phenomenon, but rather belongs to a class of mechanisms whereby proliferation is inhibited by local depletion of a factor essential for growth. Like macrophages themselves (Ottaviani, et al. *Immunol. Today* 1997;18:169-174), the IDO gene is evolutionarily ancient. An homologous gene exists in lower invertebrates, and the intron-exon structure has been highly conserved throughout 600 million years of evolution (Suzuki, et al. *Biochem. Biophys. Acta* 1996;1308:41-48). This suggests that tryptophan degradation is an effective and important strategy.

A key assumption implicit in the hypothesis is that macrophages in vivo are able to create a local microenvironment in which the tryptophan concentration is very low, despite the availability of tryptophan in the bloodstream. In theory, this should be possible because the rate of tryptophan delivery is limited by diffusion through the interstitial space. Burke, et al, have directly tested this assumption by measuring tryptophan concentrations in tumor xenografts which had been induced to express IDO by IFNγ (Burke, et al. *Int. J. Cancer* 1995;60:115-122). These authors found an approximately 80% reduction in tumor tryptophan in IFNγ-treated animals compared to controls, indicating that the rate of local degradation did indeed exceed the rate of delivery.

The IDO enzyme is known from published literature to be expressed in syncytiotrophoblast cells of the human placenta (Kamimura, et al., 1991 *Acta. Med. Okayama* 45:135-139). Syncytiotrophoblasts are fetal-derived cells which comprise the zone of contact between fetal tissues and the maternal bloodstream (and hence contact with the maternal immune system). The presence of IDO in placenta had been confusing to researchers in the field, since the placenta supplies nutrients to the fetus and it seemed paradoxical that it should actively degrade an essential nutrient such as tryptophan. Based on the in vitro and in vivo studies described herein, the hypothesis was formulated that the role of IDO in the placenta was to suppress T cell responses against the genetically "foreign" fetus. The survival of the mammalian fetus has long been a paradox in the field of immunology (Medawar, 1953, *Symp. Soc. Exp. Biol.* 7:320-338), since half of the fetus's genes are paternally inherited, and hence should provoke an allogeneic rejection response from the maternal immune system. Based on the data herein, it was predicted that if IDO activity were inhibited in placenta the fetus would be unable to protect itself against maternal T cells, and would be rejected. As shown in Table 1, inhibition of IDO with 1-methyl-tryptophan resulted in prompt, T cell-mediated rejection of all allogeneic fetuses. There was no effect of inhibitor on genetically identical (syngeneic) control fetuses, demonstrating that the inhibitor itself was not toxic. This provided definitive support for the ability of IDO to suppress T cell responses in vivo. It also showed that IDO-expressing cells other than macrophages (in this case, trophoblasts) were able to suppress T cell responses, indicating that IDO is a broadly applicable mechanism of immune suppression. Specifically, based on the data herein, it is believed that antigen-presenting cells (such as macrophages and dendritic cells) throughout the immune system use IDO to suppress unwanted T cell responses (e.g., to self antigens).

The fetus represents a dramatic example of a solid-tissue "allograft" which is tolerated by the maternal immune system throughout gestation. Prior to the discoveries described herein, it was uncertain whether the fetus presented the transplantation antigens needed to provoke rejection, and, if it did, why the maternal immune system chose to tolerate these antigens. The data in the examples reveal that the fetus does indeed present the relevant transplantation antigens (a difference in even a single MHC gene was sufficient to provoke rejection when IDO was inhibited, see Table 3), and that the maternal immune system did not "choose" to tolerate the fetus, but rather was actively prevented from mounting a response by placental expression of IDO. Taken together, these observations lead to two categories of clinical applications:

Category 1: Since IDO and tryptophan catabolism represent a new mechanism of T cell suppression, the introduction of the IDO gene by transgenesis, the use of pharmacologic inducers of IDO enzyme activity, or the direct introduction of IDO or IDO-like enzymatic activity as purified proteins into relevant sites, can all be used for local immunosuppression.

Category 2: Since inhibition of IDO is able to restore T cell responses which would otherwise be suppressed (as in the pregnancy model described herein), pharmacologic inhibitors of the IDO enzyme could be used to restore desirable T cell responses which are normally suppressed by IDO.

With regard to Category 1 (use of IDO as an immunosuppressant), the most direct application is to simply inject or otherwise deliver the purified IDO enzyme as a local immunosuppressive agent. However, because IDO contains a heme prosthetic group and requires a complex regenerating system in order to avoid auto-oxidation in vitro (Sono, et al., 1980. *J. Biol. Chem.* 255:1339-1345), it may be difficult to employ the purified enzyme directly as a pharmacologic agent. A strategy to surmount this difficulty is to use purified bacterial enzymes such as indolyl-3-alkane alpha-hydroxylase, which have IDO-like tryptophan-degrading activity and which have been shown to function in purified form (U.S. Pat. Nos. 5,723,325 and 5,244,807 to Murtfeldt, et al).

A second approach is to confer IDO enzymatic activity in a tissue-specific manner by the use of IDO as a transgene under an inducible or constitutive promoter. There is currently significant interest in developing genetically modified animals (e.g., swine) to serve as donors for solid organ xenotransplantation (Saadi and Platt 1998 *Life Sci.* 62:365-387). Based on the data herein demonstrating the role of IDO in preventing rejection of the allogeneic fetal "allograft," the use of MO as a transgene (either as a germline transgene in genetically modified animals, or delivered by transfection into human organs) can be applied to xenogeneic and allogeneic human organ transplantation.

Likewise, there exists a body of literature supporting the use of genetically modified cells to convey immunosuppressive genes into specific anatomic sites of inflammation, e.g., into the synovial space in arthritic joints (Jorgensen and Gay 1998. *Immunol. Today* 19;387-391), for purposes of local immunosuppression, or systemically for purposes of inducing tolerance to subsequent allograft transplantation. These would be additional applications of IDO used as a transgene.

Finally, there is a well-established but poorly understood correlation between tryptophan metabolism and autoimmune disorders, as described further in Example 8. Based on the data herein, it is proposed that IDO suppresses autoreactive T cell activation by degrading tryptophan in local microenvironments. From this it follows that elevated systemic tryptophan levels would make it more difficult for macrophages to deplete tryptophan locally and hence suppress autoreactive T cells; whereas lowered systemic tryptophan levels would favor suppression of autoreactive T cells. Therefore, methods to lower systemic tryptophan levels by pharmacologic induction of IDO, administration of tryptophan-degrading enzymes, or ex vivo depletion of plasma tryptophan by tryptophan-degrading enzymes, could be used in the treatment of autoimmune disorders. Examples of suitable enzymes for lowering tryptophan such as indolyl-3-alkane alpha-hydroxylase, and means for ex vivo treatment of plasma to lower tryptophan levels which are abnormally elevated are described in U.S. Pat. Nos. 5,723,325 and 5,244,807 to Murtfeldt, et al.

Inhibitors of the IDO enzyme (such as 1-methyl-DL-tryptophan, β-(3-benzofuranyl)-DL-alanine, 6-nitro-L-tryptophan and β-[3-benzo(b)thienyl]-DL-alanine), or the high affinity tryptophan transporter can be used to simulate T cell mediated immune responses where these would normally be suppressed by IDO. Applications include using these agents (systemically or locally administered) to an individual to terminate pregnancy. Other applications include transfection of the IDO gene (under an inducible promoter) into tissues and cells prior to or at the time of pregnancy, to reduce the possibility of immune-mediated rejection of the fetus. Screening of tryptophan levels and/or IDO expression can be used as indicators of T cell activation or suppression and therefore predictors of miscarriage or spontaneous abortion.

Based on these studies and the underlying mechanism, it is possible to terminate, or help to sustain in some individuals, pregnancy. To terminate the pregnancy one administers an effective amount of an inhibitor of IDO, or transport of tryptophan by the high affinity tryptophan transporter. For example, an inhibitor such as 1-methyltryptophan at a dosage of 1 g/kg is effective to cause rejection and killing by macrophages. The dosage may be administered one or more times, as required, to yield the desired effect.

Compounds which Modulate Tryptophan or Tryptophan Metabolite

A number of techniques are known for obtaining compounds which can be used to modulate tryptophan or tryptophan metabolite levels. The active compounds can be divided into the following categories:

(1) IDO and other enzymes whos activity can be modulated to alter tryptophan degradation (2) The high affinity sodium-independent extremely selective tryptophan transporter and other transporters of tryptophan which can increase or decrease typtophan transport into the cell IDO is well characterized, as discussed above. Bacterial enzymes, also discussed herein, can also be used to degrade tryptophan. Tryptophan transporters are described herein and in the literature. Although the following description is primarily directed towards modulation of IDO activity, the descriptions are equally applicable for modulators of the high affinity tryptophan transporter, which can be regulated in the same manner as other transporter molecules, by turning on or off transport by completely blocking access to the transporter, or by partially blocking access, for example, by binding of the transporter with a molecule which competitively binds with tryptophan, or which has a higher binding affinity or lower dissociation constant than tryptophan. IDO is an intracellular enzyme. In order for it to affect the extracellular level of tryptophan its substrate must be transported across the macrophage cell membrane. There are many known amino acid transport systems in mammalian cells, a number of which accept tryptophan. However, none of these are specific for tryptophan, so it must compete with various other amino acids for uptake. To date, no preferential tryptophan transporter has been described in mammalian cells. Data suggests that there may exist an IFNγ-inducible, high-affinity, tryptophan-selective uptake system in MCSF-derived macrophages. It is sodium-independent, placing it in a limited category. The known sodium-independent systems are summarized in Kakuda et al. *J. Exp. Biol.* 1994; 196:93-108; McGivan et al. *Biochem. J.* 1994; 299:321-334. In some ways the macrophage transport system resembles system L. However, in cross-competition studies, the tryptophan uptake system in macrophages shows a 10- to 100-fold higher affinity for tryptophan than for the next best substrate, phenylalanine, which does not correspond to any of the known systems. System T, which also accepts tryptophan, has a much lower affinity than the system observed in macrophages (Zhou J. *Biol. Chem.* 1990; 265:17000-17004).

Assays for testing compounds for useful activity can be based solely on interaction with IDO or enzymes or the transporters involved in tryptophan metabolism ("the enzymes"), or alternatively, the assays can be based on interaction with the gene sequence encoding the enzymes. For example, antisense which binds to the regulatory sequences, and/or to the protein encoding sequences can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothiodates and methylation), then screened initially for alteration of enzyme activity in transfected or naturally occurring cells which express the enzyme, then in vivo in laboratory animals. Typically, the antisense would inhibit expression. However, sequences which block those sequences which "turn off" synthesis can also be targeted Compounds which inhibit IDO are known, as demonstrated by the examples, although not previously described for use as immunomodulators. Additional compounds which are highly selective can be obtained as follows.

Random Generation of Enzyme or Enzyme Encoding Sequence Binding Molecules.

Molecules with a given function, catalytic or ligand-binding, can be selected for from a complex mixture of random molecules in what has been referred to as "in vitro genetics" (*Szostak, TIBS* 19:89-93, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. For example, by repeated cycles of affinity chromatography and PCR amplification of the molecules bound to the ligand on the column, Ellington and Szostak (1992) estimated that 1 in $10^{10}$ RNA molecules folded in such a way as to bind a given ligand. DNA molecules with such ligand-binding behavior have been isolated (Ellington and Szostak, 1992; Bock et al, 1992).

Computer Assisted Drug Design

Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modelling systems are the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rouvinen et al., 1988 *Acta Pharmaceutica Fennica* 97, 159-166; Ripka, *New Scientist* 54-57 (Jun. 16, 1988); McKinlay and Rossmann, 1989 *Annu. Rev. Pharmacol. Toxicol.* 29, 111-122; Perry and Davies, QSAR: Quantitative Structure-Activity Relationships in Drug Design, Proceedings of the $7^{th}$ European Symposium on *QSAR held in Interlaken, Switzerland, Sep.* 5-9, 1988, pp. 189-193 (Alan R. Liss, Inc. 1989); Lewis and Dean, 1989 Proc. R. Soc. Lond. 236, 125-140 and 141-162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Tnc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Generation of Nucleic Acid regulators

Nucleic acid molecules containing the 5' regulatory sequences of the enzyme genes can be used to regulate or inhibit gene expression in vivo. Vectors, including both plasmid and eukaryotic viral vectors, may be used to express a particular recombinant 5' flanking region-gene construct in cells depending on the preference and judgment of the skilled practitioner (see, e.g., Sambrook et al., Chapter 16). Furthermore, a number of viral and nonviral vectors are being developed that enable the introduction of nucleic acid sequences in vivo (see, e.g., Mulligan, 1993 *Science,* 260, 926-932; U.S. Pat. Nos. 4,980,286; 4,868,116; incorporated herein by reference). Nucleic acid can be encapsulated in cationic liposomes which can be injected intravenously into a mammal (Zhu et al., 1993 *Science* 261, 209-211).

The 5' flanking sequences of the enzyme gene can also be used to inhibit the expression of the enzyme. For example, an antisense RNA of all or a portion of the 5' flanking region of the enzyme gene can be used to inhibit expression of the enzyme in vivo. Expression vectors (e.g., retroviral expression vectors) are already available in the art which can be used to generate an antisense RNA of a selected DNA sequence which is expressed in a cell (see, e.g., U.S. Pat. Nos. 4,868,116; 4,980,286). Accordingly, DNA containing all or a portion of the sequence of the 5' flanking region of the enzyme gene can be inserted into an appropriate expression vector so that upon passage into the cell, the transcription of the inserted DNA yields an antisense RNA that is complementary to the mRNA transcript of the enzyme gene normally found in the cell. This antisense RNA transcript of the inserted DNA can then base-pair with the normal MRNA transcript found in the cell and thereby prevent the mRNA from being translated. It is of course necessary to select sequences of the 5' flanking region that are downstream from the transcriptional start sites for the enzyme gene to ensure that the antisense RNA contains complementary sequences present on the MRNA.

Antisense RNA can be generated in vitro also, and then inserted into cells. Oligonucleotides can be synthesized on an automated synthesizer (e.g., Model 8700 automated synthesizer of Milligen-Biosearch, Burlington, MA or ABI Model 380B). In addition, antisense deoxyoligonucleotides have been shown to be effective in inhibiting gene transcription and viral replication (see e.g., Zamecnik et al., 1978 *Proc. Natl. Acad. Sci. USA* 75, 280-284; Zamecnik et al., 1986 *Proc. Natl. Acad. Sci.*, 83, 4143-4146; Wickstrom et al., 1988 *Proc. Natl. Acad. Sci. USA* 85, 1028-1032; Crooke, 1993 *FASEB J.* 7, 533-539. Inhibition of expression of a gene by antisense oligonucleotides is possible if the antisense oligonucleotides contain modified nucleotides (see, e.g., Offensperger et. al., 1993 *EMBO J.* 12,1257-1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., 1988 *Proc. Natl. Acad. Sci. USA* 85, 7079-7083 (synthesis of antisense oligonucleoside phosphoramidates and phosphorothioates to inhibit replication of human immunodeficiency virus-1); Sarin et al., 1989 *Proc. Natl. Acad. Sci. USA* 85, 7448-7451 (synthesis of antisense methylphosphonate oligonucleotides); Shaw et at, 1991 *Nucleic Acids Res.* 19, 747-750 (synthesis of 3' exonuclease-resistant oligonucleotides containing 3' terminal phosphoroamidate modifications); incorporated herein by reference).

The sequences of the 5' flanking region of enzyme gene can also be used in triple helix (triplex) gene therapy. Oligonucleotides complementary to gene promoter sequences on one of the strands of the DNA have been shown to bind promoter and regulatory sequences to form local triple nucleic acid helices which block transcription of the gene (see, e.g., 1989 Maher et al., *Science* 245, 725-730; Orson et al., 1991 *Nucl. Acids Res.* 19, 3435-3441; Postal et al., 1991 *Proc. Natl. Acad. Sci. USA* 88, 8227-8231; Cooney et al., 1988 *Science* 241, 456-459; Young et al., 1991 *Proc. Natl. Acad. Sci. USA* 88, 10023-10026; Duval-Valentin et al., 1992 *Proc. Natl. Acad. Sci. USA* 89, 504-508; 1992 Blume et al., *Nucl. Acids Res.* 20, 1777-1784; 1992 Grigoriev et al., *J. Biol. Chem.* 267, 3389-3395.

Both theoretical calculations and empirical findings have been reported which provide guidance for the design of oligonucleotides for use in oligonucleotide-directed triple helix formation to inhibit gene expression. For example, oligonucleotides should generally be greater than 14 nucleotides in length to ensure target sequence specificity (see, e.g., Maher et al., (1989); Grigoriev et al., (1992)). Also, many cells avidly take up oligonucleotides that are less than 50 nucleotides in length (see e.g., Orson et al., (1991); Holt et al., 1988 *Mol. Cell. Biol.* 8, 963-973; Wickstrom et al., 1988 *Proc. Natl. Acad. Sci. USA* 85, 1028-1032). To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (e.g., via a pentamethylene bridge); again without loss of sequence specificity (Maher et al., (1989); Grigoriev et al., (1992)).

Methods to produce or synthesize oligonucleotides are well known in the art. Such methods can range from standard enzymatic digestion followed by nucleotide fragment isolation (see e.g., Sambrook et al., Chapters 5, 6) to purely synthetic methods, for example, by the cyanoethyl phosphoramidite method using a Milligen or Beckman System 1Plus DNA synthesizer (see also, Itakura et al., in *Ann. Rev. Biochem.* 1984 53, 323-356 (phosphotriester and phosphite-triester methods); Narang et al., in *Methods Enzymol.*, 65, 610-620 (1980) (phosphotriester method).

Preparation of Enzyme Fragments

Compounds which are effective for blocking binding of the enzyme can also consist of fragments of the enzymes, expressed recombinantly and cleaved by enzymatic digest or expressed from a sequence encoding a peptide of less than the full length enzyme. It is a routine matter to make appropriate enzyme fragments, and test for inhibition of activity of the enzyme in the presence of the fragments. The preferred fragments are of human origin, in order to minimize potential immunological response. The peptides can be as short as five to eight amino acids in length and are easily prepared by standard techniques. They can also be modified to increase in vivo half-life, by chemical modification of the amino acids or by attachment to a carrier molecule or inert substrate. The peptides can also be conjugated to a carrier protein such as keyhole limpet hemocyanin by its N-terminal cysteine by standard procedures such as the commercial ImJect kit from Pierce Chemicals or expressed as a fusion protein, which may have increased efficacy. As noted above, the peptides can be prepared by proteolytic cleavage of the enzymes, or, preferably, by synthetic means. These methods are known to those skilled in the art. An example is the solid phase synthesis described by J. Merrifield, 1963 *J. Am. Chem. Soc.* 85, 2149-2154, used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having identical sequence to the enzymes described herein, or substitutions or additions of amino acids, which can be screened for activity as described above.

The peptide can also be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Peptides containing cyclopropyl amino acids, or amino acids derivatized in a similar fashion, can also be used. These peptides retain their original activity but have increased half-lives in vivo. Methods known for modifying amino acids, and their use, are known to those skilled in the art, for example, as described in U.S. Pat. No. 4,629,784 to Stammer.

Pharmaceutical Compositions

Compounds which alter enzyme activity and/or tryptophan transport are preferably administered in a pharmaceutically acceptable vehicle. Suitable pharmaceutical vehicles are known to those skilled in the art. For parenteral administration, the compound will usually be dissolved or suspended in sterile water or saline. For enteral administration, the compound will typically be administered in a tablet or capsule, which may be enteric coated, or in a formulation for controlled or sustained release. Many suitable formulations are known, including polymeric or protein microparticles encapsulating drug to be released, ointments, gels, or solutions which can be used topically or locally to administer drug, and even patches, which provide controlled release over a prolonged period oftime. These can also take the form of implants. For example prevention of pregnancy could be obtained by administration intravaginally of a compound increasing tryptophan, for example, by inhibiting IDO, thereby resulting in killing of the sperm or fertilized egg almost immediately.

Generation of Transgenic Animals for Screening

With the knowledge of the cDNA encoding the enzyme and regulatory sequences regulating expression thereof, it is possible to generate transgenic animals, especially rodents, for testing the compounds which can alter enzyme expression, translation or function in a desired manner.

There are basically two types of animals which are useful: those not expressing functional enzyme, and those which overexpress enzyme, either in those tissues which already express the protein or in those tissues where only low levels are naturally expressed. The animals in the first group are preferably made using techniques that result in "knocking out" of the gene for enzyme, although in the preferred case this will be incomplete, either only in certain tissues, or only to a reduced amount. These animals are preferably made using a construct that includes complementary nucleotide sequence to the enzyme gene, but does not encode functional enzyme, and is most preferably used with embryonic stem cells to create chimeras. Animals which are heterozygous for the defective gene can also be obtained by breeding a homozygote normal with an animal which is defective in production of enzyme.

The animals in the second group are preferably made using a construct that includes an unregulated promoter or one which is modified to increase expression as compared with the native promoter. The regulatory sequences for the enzyme gene can be obtained using standard techniques based on screening of an appropriate library with the cDNA encoding enzyme. These animals are most preferably made using standard microinjection techniques.

These manipulations are performed by insertion of cDNA or genomic DNA into the embryo using microinjection or other techniques known to those skilled in the art such as electroporation, as described below. The DNA is selected on the basis of the purpose for which it is intended: to inactivate the gene encoding an enzyme or to overexpress or express the gene encoding enzyme. The enzyme encoding gene can be modified by homologous recombination with a DNA for a defective enzyme, such as one containing within the coding sequence an antibiotic marker, which can then be used for selection purposes.

Animals suitable for transgenic experiments can be obtained from standard commercial sources. These include animals such as mice and rats for testing of genetic manipulation procedures, as well as larger animals such as pigs, cows, sheep, goats, and other animals that have been genetically engineered using techniques known to those skilled in the art. These techniques are briefly summarized below based principally on manipulation of mice and rats. The procedures for manipulation of the embryo and for microinjection of DNA are described in detail in Hogan et al. Manipulating the mouse embryo, Cold Spring Harbor Laboratory, Cold Spring Harbor, N.Y. (1986), the teachings of which are incorporated herein. These techniques are readily applicable to embryos of other animal species, and, although the success rate is lower, it is considered to be a routine practice to those skilled in this art. Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987), the teachings of which are incorporated herein. Selection of the desired clone of transgene-containing ES cells is accomplished through one of several means. In cases involving sequence specific gene integration, a nucleic acid sequence for recombination with the enzyme gene or sequences for controlling expression thereof is co-precipitated with a gene encoding a marker such as neomycin resistance. Transfection is carried out by one of several methods described in detail in Lovell-Badge, in *Teratocarcinomas and embryonic stem cells, a practical approach*, ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. DNA molecules introduced into ES cells can also be integrated into the chromosome through the process of homologous recombination, described by Capecchi, (1989).

Once the transgenic animals are identified, lines are established by conventional breeding and used as the donors for tissue removal and implantation using standard techniques for implantation into humans.

Therapeutic Applications

The examples described herein demonstrate that tryptophan depletion and/or catabolism is the mechanism by which macrophages suppress T cell activation, using in vitro human and in vivo transgenic mouse models; defines the developmental regulation of the IDO gene during hematopoietic differentiation of macrophages and dendritic cells; and defines the functional characteristics and developmental regulation of the tryptophan transport pathway in immunosuppressive macrophages. These studies define a new and previously unsuspected role for tryptophan metabolism to immune regulation.

Pharmaceutical compositions based on these discoveries rely on either increasing tryptophan concentrations (and thereby decreasing tryptophan metabolite concentrations) or decreasing tryptophan concentrations (and thereby increasing tryptophan metabolite concentrations). Inhibitors of IDO increase tryptophan concentrations (and thereby decrease tryptophan metabolite concentrations), increasing T cell activation. IDO decreases tryptophan concentrations (and thereby increases tryptophan metabolite concentrations), decreasing T cell activation.

Inhibitors of the IDO enzyme, such as 1-methyl-DL-tryptophan, β-(3-benzofuranyl)-DL-alanine, β-[3-benzo(b)thienyl]-DL-alanine, and 6-nitro-L-tryptophan, can be used to simulate T cell mediated immune responses where these would normally be suppressed by IDO. Inhibitors of other enzymes involved in tryptophan metabolism or degradation can also be used. Applications include using these agents (systemically administered) as vaccine adjuvants to increase the immunogenicity of administered antigens; using the agents for immunotherapy of malignancy, including as an adjuvant for therapeutic tumor-cell vaccines, and as an adjunct to cytokine-based immunotherapy of malignancy; and using these agents to help reverse the immunosuppressed state found in AIDS since IDO is known to be induced during HIV infection; co-administering IDO inhibitors with HIV vaccine to enhance the efficacy of HIV vaccines since IDO is induced in macrophage-lineage cells by HIV infection; and generally for any setting in which IDO mediates unwanted suppression of a desired immune response.

Alternatively, recombinant IDO can be used as a means of systemic or local T cell suppression. Applications include transfection of the IDO gene (under an inducible promoter) into tissues and cells prior to allotransplantation, in order to allow them to protect themselves from rejection by the host, for example, by retroviral or other transfer of the IDO gene into allogeneic solid-organ grafts (kidney, etc.); by transgenic expression of the gene in porcine or other animals designed as donors for xeno-transplantation, to prevent rejection; or by retroviral or other transfer into cell preparations intended for transplantation (eg, pancreatic islet cells for therapy of diabetes mellitus).

Applications also include using these agents (systemically or locally administered) to an individual to terminate pregnancy. Other applications include transfection of the IDO gene (under an inducible promoter) into tissues and cells prior to or at the time of pregnancy, to reduce the possibility of immune-mediated rejection of the fetus. To terminate the pregnancy one administers an effective amount of an inhibitor of IDO, or transport of tryptophan by the high affinity tryptophan transporter. For example, an inhibitor such as 1-methyltryptophan at a dosage of 1 g/kg is effective to cause rejection and killing by macrophages. The dosage may be administered one or more times, as required, to yield the desired effect.

Screening of tryptophan levels and/or IDO expression can be used as indicators of T cell activation or suppression. Screening of tryptophan levels and/or IDO expression can be used as indicators of T cell activation or suppression and therefore predictors of miscarriage or spontaneous abortion. Testing for IDO expression tumor biopsies can be used to determine the suitability of the cancer for IDO-targeted therapy.

The present invention will be further understood by reference to the following non-limiting examples.

EXAMPLE 1

Macrophage-induced Suppression

As described in Munn, et al. J. Immunol. 1996;156:523-532, a number of possible mechanisms for macrophage-induced suppression were initially examined. None of those tested, including the fas/fas-L system, nitric oxide, free radicals, prostaglandins, and inhibitory cytokines, could account for the phenomenon. Studies demonstrated the following regarding macrophage inhibition of T cell proliferation:

(1) MCSF-derived macrophages inhibit the mitogen-induced proliferation of T cells, and this is a dominant effect—i.e., it is not rescued by adding non-inhibitory APCs.
(2) The T cells initiate early activation, as assessed by activation-related G1 phase genes (IL-2 receptor, cdc2, cyclin A), but arrest prior to the first G1/S boundary. This arrest is not a stable condition, and most of the lymphocytes progressively die off.
(3) The suppressive effect was developmentally regulated by MCSF and IFNγ. It was not present in fresh monocytes, emerged progressively over 4-5 days of differentiation in MCSF, and was prevented if the monocytes were exposed to IFNγ (even transiently) prior to differentiation. IFNγ has a dual action in macrophage differentiation. If monocytes are exposed to IFNγ prior to differentiation it functions as a developmental regulator, and the monocytes will not subsequently acquire the suppressive phenotype—even in the presence of MCSF. However, if macrophages are exposed to IFNγ after differentiation, it causes activation but does not alter the MCSF-induced phenotype. Thus, the nature of the response to IFNγ is determined by the developmental state of the macrophage.
(4) There was no evidence for participation of nitric oxide, reactive oxygen species, TNF, TGFβ, prostaglandins, IL-1R antagonist, or IL-10. The mechanism of inhibition appeared contact dependent. Inhibition could not be reproduced by conditional medium (up to 50% v/v), and was abrogated when T cells were separated from macrophages by a semipermeable membrane. The contact-dependence is understandable in light of the data indicating a requirement for CD40/CD40L in order to produce full activation of tryptophan degradation.

EXAMPLE 2

Tryptophan Degradation by MCSF-derived Macrophages

Medium in macrophage-lymphocyte co-cultures is selectively depleted of tryptophan. Conditioned medium was generated from co-cultures of macrophages plus T cells activated with mitogen (two different mitogens, anti-CD3 antibody and SEB, gave equivalent results; the data presented are from anti-CD3). Fresh lymphocytes were suspended in conditioned medium and activated with additional mitogen. Care was taken to exclude all traces of fresh medium.

As shown in FIG. 1, conditioned medium completely failed to support T cell proliferation (less than 1% of the proliferation in fresh medium). In contrast, control conditioned media from macrophages alone, from co-cultures of macrophages and T cells without mitogen, and from T cells activated with fresh monocytes instead of macrophages, all supported T cell proliferation comparably to fresh medium (90-140%) of control, n=3-4 in each group, p=NS by ANOVA, see Munn et al. *J. Immunol.* 1996;156:523-532 for representative data.

Selective add-back studies showed that the deficiency lay in an essential amino acid. Supplementation with individual amino acids (FIG. 1) showed that tryptophan was depleted in conditioned medium. The addition of tryptophan to conditioned medium fully restored T cell proliferation, indicating that tryptophan was the only deficient component. Consistent with this, HPLC analysis of conditioned media showed that the levels of other essential amino acids were similar to fresh medium (some concentrations were higher, presumably due to protein catabolism).

Figure 2:
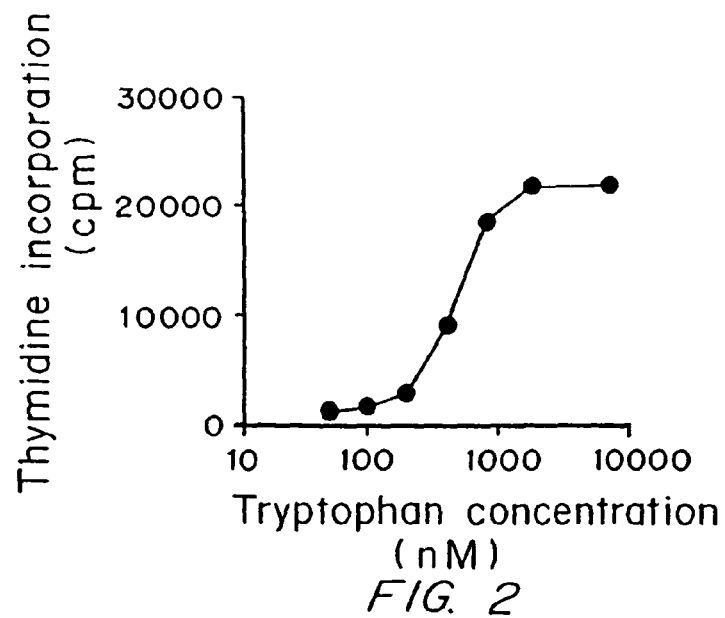
FIG. 2 is a graph of thymidine incorporation as a function of tryptophan concentration (nM) showing the dose-response relationship to tryptophan. Tryptophan was titrated in co-culture conditioned medium as described in FIG. 1., and proliferation of T cells measured at 72 hrs. SD was less than 10% and error bars are omitted for clarity.

As shown in FIG. 2, titration of reagent tryptophan in conditioned medium gave a half-maximal concentration of approximately 500 nM for T cell proliferation (compared to a normal level in RPMI of 25 µM). These studies also showed that as little as 50 nM was sufficient to initiate low but readily detectable T cell proliferation, indicating that tryptophan had been reduced below this range. Consistent with this, direct measurement of tryptophan in conditioned medium was below the detection limit for our assay, which was 50 nM.

Figure 3:
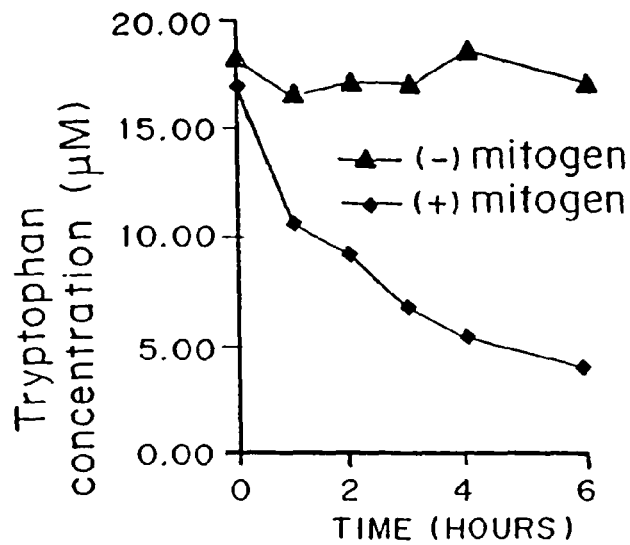
FIG. 3 is a graph of tryptophan concentration (micromoles) over time in hours showing the elimination kinetics of tryptophan in co-cultures. MCSF-derived macrophages were cultured for 24 hrs with autologous T cells, with or without anti-CD3 mitogen. The medium was replaced with fresh medium, and supernatant from replicate cultures harvested at the times shown. The concentration of tryptophan was determined by the formaldehyde/$FeCl_2$ fluorescence assay. Error bars (less than 10%) are omitted for clarity.

Depletion of tryptophan is rapid. Macrophages were co-cultured with T cells and mitogen for 24 hrs to allow up-regulation of the tryptophan-depletion pathway, then fresh medium was added and the kinetics of elimination measured. As shown in FIG. 3, tryptophan was eliminated by first-order kinetics with a half-life of approximately 2 hours. The initial rate of elimination (when tryptophan was not limiting) was up to 20,000 pmol/$10^6$ cells/hr. By way of comparison, fresh monocytes stimulated with IFNγ (a standard model of IDO induction) degraded tryptophan at approximately 200 pmol/$10^6$ cells/hr, which is consistent with the literature. This rapid rate of tryptophan depletion could not be attributed to consumption by cellular metabolism. Despite their high metabolic activity, macrophages alone depleted tryptophan at a barely detectable rate (less than 5% of the activated rate, FIG. 3). It also did not reflect sequestration of free tryptophan within macrophages, since the preliminary validation studies had shown that tryptophan was undetectable in culture supernatants whether macrophages were intact or lysed prior to performing the assay.

EXAMPLE 3

Figure 4A:
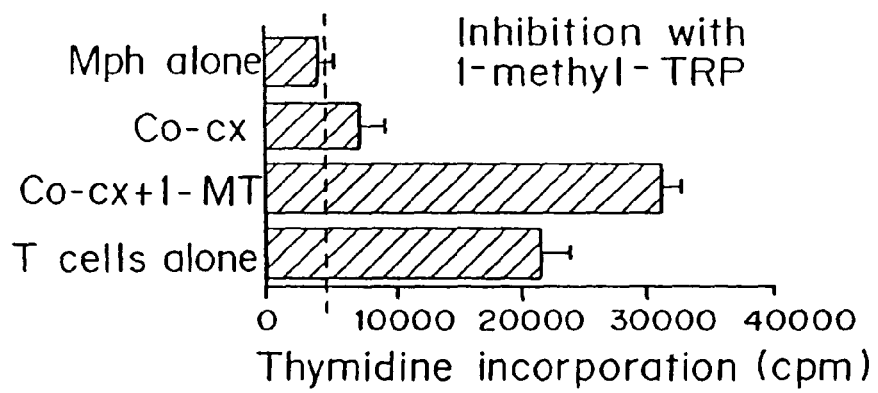
FIG. 4A and 4B are graphs showing inhibition of the IDO enzyme abrogates suppression. Co-cultures of MCSF-derived Mφs and T cells with anti-CD3 mitogen were supplemented either with the IDO inhibitor-1-methyl-tryptophan (FIG. 4A), or with 10× the normal concentration of tryptophan (FIG. 4B). Proliferation was measured after 72 hrs by thymidine incorporation. The level of background proliferation contributed by macrophages is indicated by the dotted line.

Inhibition of Tryptophan degradation by MCSF-derived Macrophages Prevents Suppression of T Cells Inhibition of tryptophan degradation prevents Macrophage-mediated suppression of Tcells. The data predicts that pharmacologic inhibitors of IDO should prevent suppression. One potent inhibitor of IDO is the 1-methyl derivative of tryptophan (Cady, et al. *Arch. Biochem. Biophys.* 1991;291: 326-333). As shown in FIG. 4A, the presence of 1-methyl-tryptophan effectively prevented macrophages from suppressing T cell activation. These data were selected in order to clearly demonstrate that suppression can be abrogated, but in most experiments the effect of 1-methyl-tryptophan has been less complete (typically 59-60% reversal of suppression). This was not unexpected, given the extremely high level of enzyme activity and the fact that 1-methyl-tryptophan is a competitive, rather than an irreversible, inhibitor. In order to fully abrogate macrophage-mediated suppression it will be necessary to simultaneously block the induction of the enzyme and to pharmacologicially inhibit its activity.

Figure 4B:
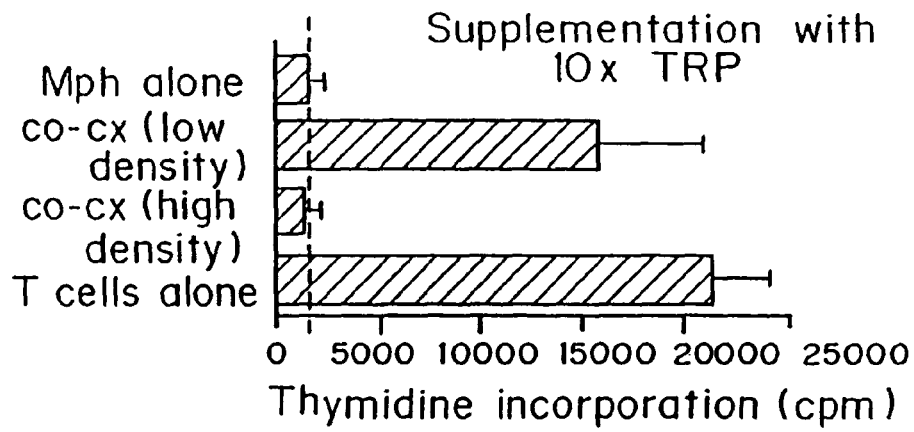

Macrophages can overcome high concentrations of tryptophan. A second test of the mechanism was to supplement the culture medium with additional tryptophan to reverse the inhibitory effect of IDO. Tryptophan supplementation alone was never as effective as 1-methyl-tryptophan, and sometimes was entirely ineffective, and as shown in FIG. 4B, appears to be related to the seeding density of macrophages and T cells. At low densities, supplemental tryptophan effectively reversed suppression, but at high densities the macrophages remained able to suppress. The effect of seeding density is believed to reflect the limited ability of diffusion to deliver tryptophan to the T cells and macrophages.

EXAMPLE 4

Effect of Cytokines on Macrophage Tryptophan Degradation

Macrophage tryptophan degradation is synergistically induced by signals of early Tcell activation. The rapid depletion of tryptophan by macrophages was not induced by resting T cells, but occurred only when the T cells attempted to activate (cf. FIG. 3). This implied that the macrophages were detecting some sign of T cell activation which triggered tryptophan degradation. In light of the studies implicating IFNγ as a major regulator of the IDO gene, it was predicted that T cell-derived IFNγ would be the signal for tryptophan degradation. However, when dose-response titration was performed of recombinant IFNγ on MCSF-derived macrophages, it was found that IFNγ concentrations of 100 U/ml or more were required for maximal induction, and even then the level of enzyme activity did not reach those achieved by co-culture with activated T cells.

Figure 5:
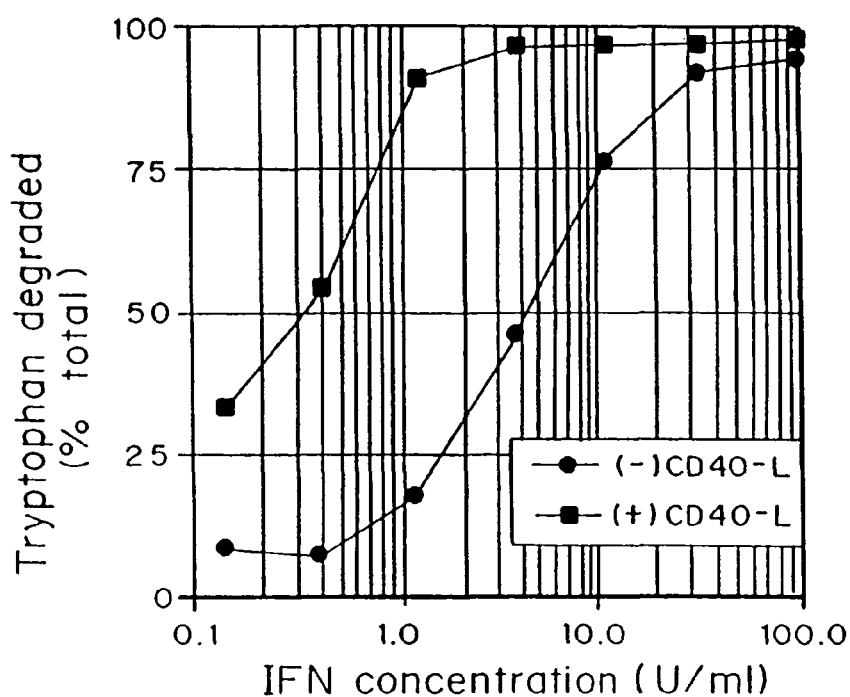
FIG. 5 is a graph of tryptophan degradation (% total) versus interferon concentration (U/ml) showing that CD40-L acts synergistically with IFNγ to induce IDO activity. MCSF-derived macrophages were activated for 24 hrs with various concentrations of recombinant IFNγ, in the presence or absence of recombinant CD40-L trimer. At the end of the activation period the tryptophan remaining in the cultures was assayed as described for FIG. 3. SD was less than 10%.

CD40L is upregulated early in T cell activation and it is known to act synergistically with IFNγ in signaling macrophages for other functions. The response of MCSF-derived macrophages to IFNγ in the presence or absence of recombinant CD40L (prepared as a homo-trimer in order to signal via CD40 in soluble fonn, gift of Bill Fanslow, Immunex Corporation) was compared. The addition of CD40L alone had little effect on enzyme activity, but as shown in FIG. 5 it displayed marked synergy when combined with IFNγ. The effect of CD40L was to shift the dose-response curve of IFNγ one to two orders of magnitude, so that significant response now occurred at IFNγ concentrations as low as 1 U/ml. Thus, two signals normally delivered by T cells to APC early in the course of activation combined to induce tryptophan degradation in MCSF-derived M+s.

Figure 6:
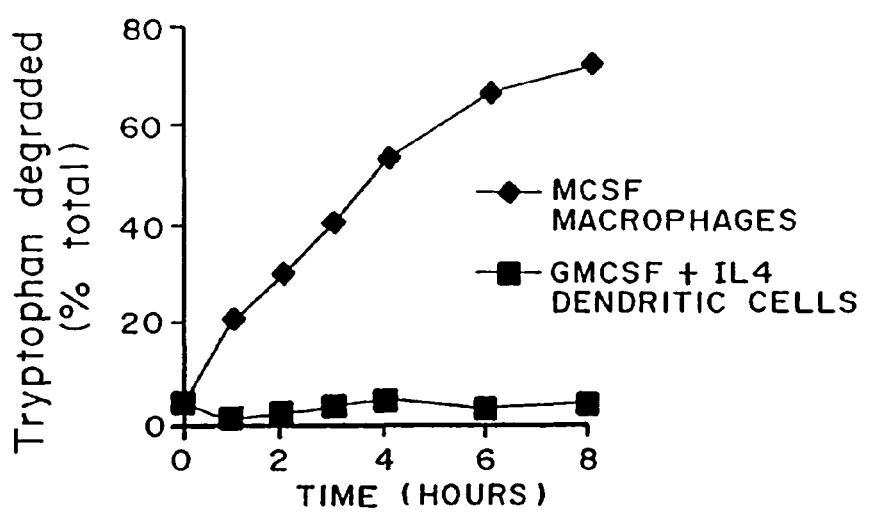
FIG. 6 is a graph of tryptophan degradation (% total) over time (hours) for showing developmental regulation of inducible IDO activity. Monocytes were allowed to differentiate in either MCSF or GMCSF+IL-4 for 5 days, then activated by sequential exposure to CD40-L and IFNγ. Following activation, the medium was replaced with fresh medium and the rate of tryptophan catabolism measured over 8 hrs. SD was less than 10%.

The responsiveness of tryptophan metabolism to IFNγ and CD40L is developmentally regulated. It was then determined if all monocyte-derived cells degraded tryptophan in response to these signals, or whether it was specifically associated with the MCSF phenotype. To generate a non-suppressive phenotype for comparison, monocytes were cultured for 5 days GMCSF+IL-4, which produces cells that closely resemble tissue dendritic cells, and which are potent activators of T cells. For clarity, these cells are referred to as dendritic cells and MCSF-derived cells as macrophages. As shown in FIG. 6, dendritic cells showed minimal tryptophan degradation in response to IFNγ and CD40L, in contrast to MCSF-derived macrophages. Thus, the response to IFNγ was not simply a feature of differentiated monocytes, but was regulated by the cytokine milieu present during terminal differentiation. Interestingly, when the cytokines were added sequentially, the effect of CD40L on dendritic cells was to further inhibit any residual induction of tryptophan degradation in response to IFNγ, exactly the opposite of its effect on macrophages.

EXAMPLE 5

The Tryptophan Transport System in Macrophages

Figure 7A:
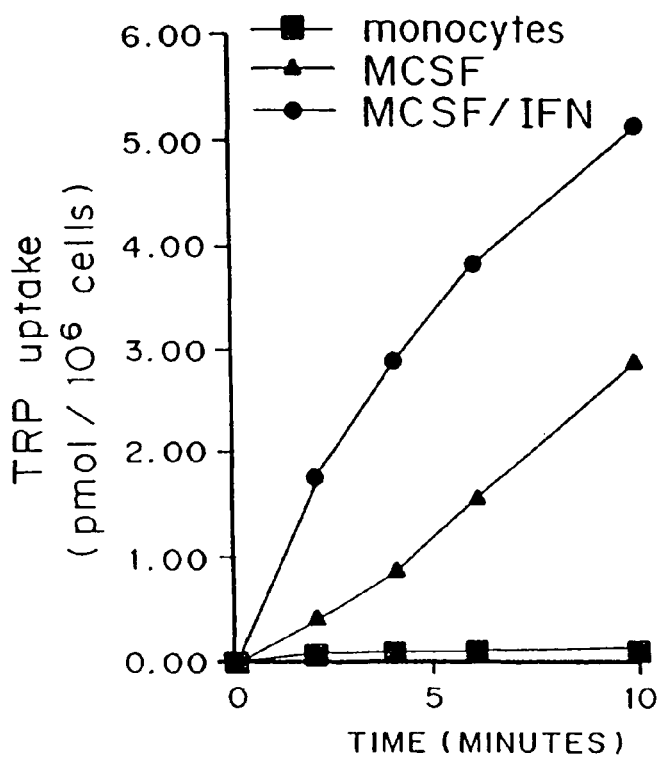
FIGS. 7A and 7B are graphs of tryptophan uptake (pmol/$10^6$ cells) over time (min) showing inducible transport of tryptophan into macrophages.

Transport of tryptophan into Macrophages is developmentally regulated. Whether the upregulation of tryptolian degradation was accompanied by increased or decreased tryptophan transport into macrophages was then determined. As shown in FIG. 7A, following differentiation MCSF-derived macrophages showed a markedly increased ability to take up tryptophan, 10 to 20-fold greater than fresh monocytes, which was further induced by activation with IFNγ.

Figure 7B:
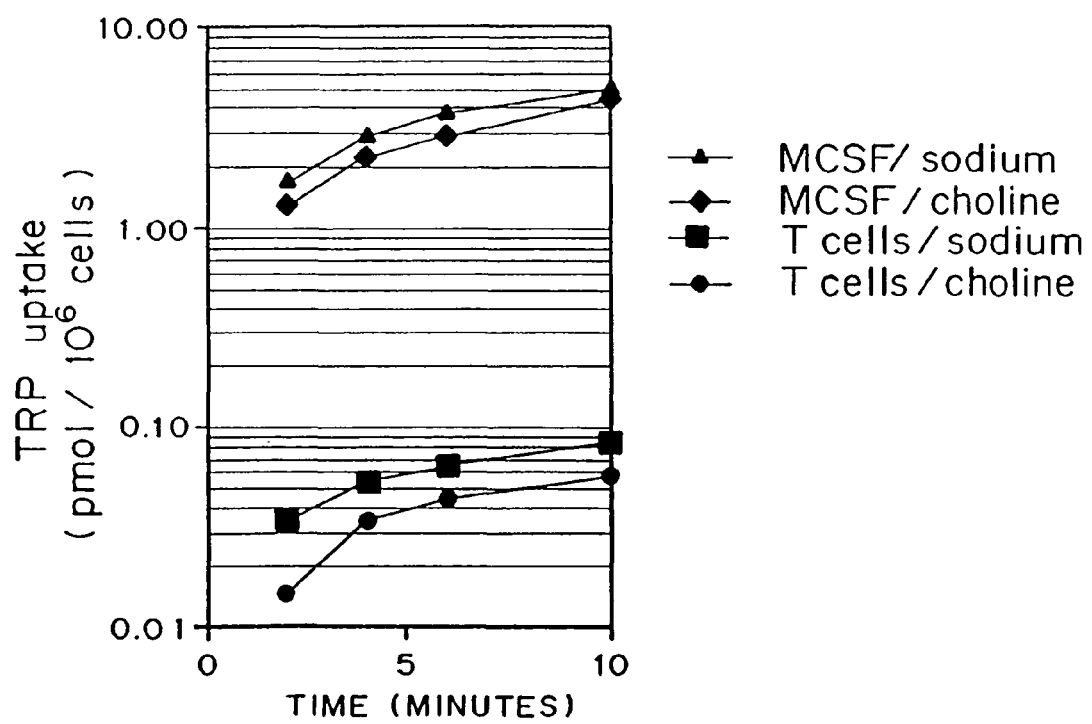
Figure 8A:
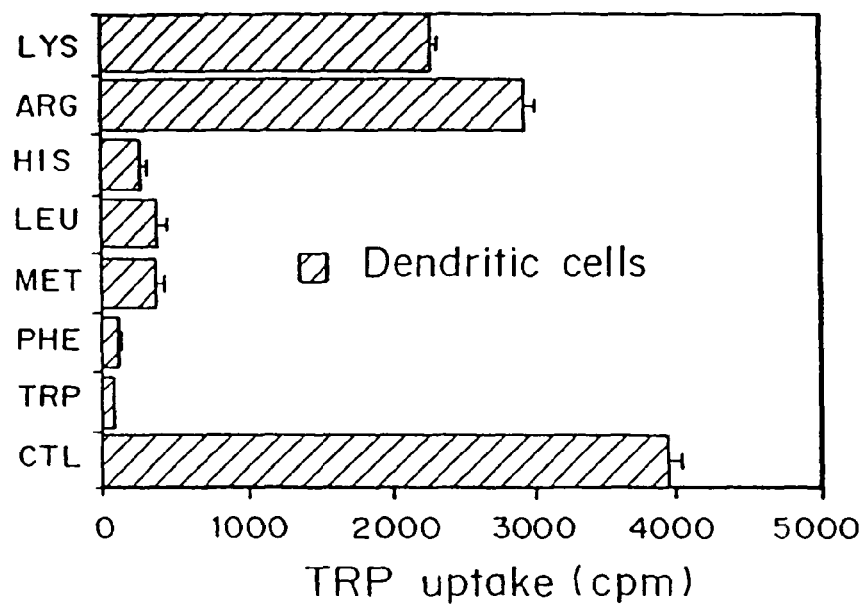
FIGS. 8A and 8B are graphs of tryptophan uptake (cpm) in the presence of various competing unlabeled amino acids for dendritic cells (FIG. 8A) and MCSF macrophages (FIG. 8B) showing sodium-independent transport of tryptophan in MCSF-derived macrophages does not have the characteristics of system L. Monocytes were allowed to differentiate for 5 days in the presence of either GMCSF+IL-4 (dendritic cells, FIG. 8A) or MCSF (macrophages, FIG. 8B). Sodium-independent tryptophan transport was assayed as described in FIG. 7 in the presence of various competing unlabeled amino acids (8 mM each).
Figure 8B:
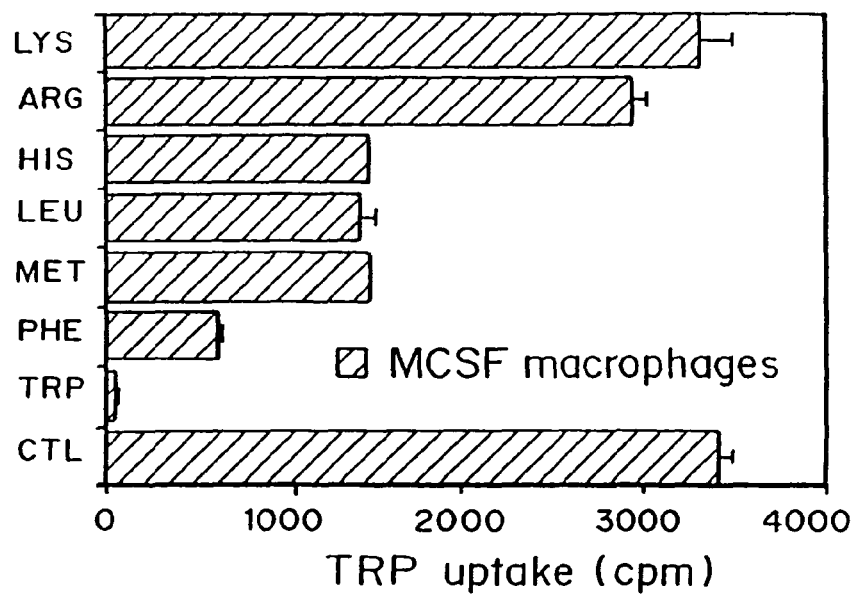

Tryptophan transport in MCSF-derived Macrophages shovs a preferential affinity for tryptophan. To characterize the tryptophan transport system, whether uptake was dependent on the sodium gradient was then determined. Preliminary studies had shown that tryptophan transport in fresh monocytes was sodium dependent (less than 10% of transport was sodium-independent). However, as shown in FIG. 7B, the majority of the tryptophan transport in macrophages was independent of sodium. This sodium-independent system was then characterized using cross-competition studies. As expected, T cells showed a pattern consistent with system L, with tryptophan uptake being inhibited by aromatic and neutral amino acids, but not lysine or arginine (FIG. 8A). In contrast, however, tryptophan uptake by MCSF macrophages (FIG. 8B) was only partially inhibited by neutral amino acids, and even phenylalanine could not fully block it.

As shown in FIG. 9, titration studies indicated that phenylalanine (the best competitor) was 10- to 100-fold less effective than tryptophan in competing for uptake, based on relative $IC_{50}$. Tyrosine, leucine, and the system L-specific substrate 2-amino-2-norborane-carboxylic acid (BCH) were even less effective competitors. Significantly, when system L was inhibited by 8 mM BCH, there still remained 30-50% of the total tryptophan transport available (depending on the experiment). Taken together these data suggested that a high-affinity, non-system L transport pathway might be present.

EXAMPLE 6

In vivo Studies of the Role of IDO and Tryptophan Degradation on Activation of T Cells Peripheral deletion of autoreactive T cells in vivo is accompanied by evidence of tryptophan degradation. Whether there was evidence that IDO was involved in peripheral tolerance in vivo was then assessed. Since IDO activity at the single cell level cannot be measured in vivo, a model in which a large number of autoreactive T cells underwent synchronous activation and deletion was needed. This would allow one to follow the kynurinine breakdown products released systemically when IDO degrades tryptophan (Meyer, et al. *J. Lab. Clin. Med.* 1995;126:530-540). Dr. Mellor had developed such a model by creating mice transgenic for a T cell receptor recognizing the H-2K$^b$ (MHC class I) antigen. When these T cells are adoptively transferred into a syngeneic animal made transgenic for the target antigen, they become functionally autoreactive. As described in Tarazona, et al. *Intl. Immunol.* 1996;8:351-358, these autoreactive T cells undergo a transient period of activation, but then are rapidly eliminated (day 4-5) without causing disease. This occurs despite the fact that they are not subject to rejection by the host (being syngeneic), and are eliminated only in animals where they encounter their antigen. This therefore represents a useful model of synchronous deletion of autoreactive T cells.

Splenocytes from T cell receptor-transgenic mice ($4 \times 10^7$ cells) were adoptively transferred by tail vein injection into antigen-transgenic mice. On day 3 (at the beginning of the rapid expansion phase), the recipient animals were sacrificed and serum was obtained. Pre-transfer sera were used as controls. As shown in FIG. 10, mice which had received autoreactive T cells showed a marked elevation in serum kynurinine compared to controls. Thus, the expansion and elimination of autoreactive T cells in vivo was accompanied by evidence of significant tryptophan catabolism, consistent with activation of IDO.

Whether in vivo inhibition of the IDO enzyme with 1-methyl tryptophan (as described in vitro in FIG. 4A) would alter the kinetics of activation or elimination of autoreactive T cells in the mouse model was then measured. As shown in FIG. 11, continuous infusion of 1-methyl tryptophan (via subcutaneously implanted timed-release pellets, 1000 mg/kg/day) resulted in significantly enhanced activation of the adoptively transferred T cells. These results strongly support a role for IDO in suppressing T cell activation in vivo.

EXAMPLE 7

MCSF and Tissue Macrophages

Clinically, there exists an ill-defined association between altered tryptophan metabolism and autoimmune disorders. Patients receiving L-5-hydroxytryptophan for neurologic disorders experienced a high frequency of a scleroderma-like illness (Sternberg et al. *N Engl. J. Med.* 1980; 303:782-787). Individuals who ingested certain preparations of L-tryptophan contaminated with toxic tryptophan derivatives (1-1' ethylidenebis-[tryptophan]) experienced the eosinphilia-myalgia syndrome (Belongia et al. *N.E. Engl. J. Med.* 1990; 323:357-365; Mayeno et al. *Science* 1990; 250:1707-1708), which included excessive T cell activation. There is even a case report of simple dietary supplementation with tryptophan leading to multiple autoimmune disorders (Morgan, et al. *Br. J. Dermatol.* 1993; 128:581-583).

The osteopetrotic (op/op) mouse lacks functional MCSF, and has a selective deficiency in specific sublets of tissue macrophages (Cecchini, et al. *Development* 1994; 120:1357-1372). It has nonnal dendritic cell development and nounal T cell responses to foreign antigens (Begg et al. *J. Exp. Med.* 1993; 177:237-242) indicating that these functions are not MCSF-dependent. Interestingly, in one well-established model of spontaneous autoimmunity, the NOD mouse, the macrophages have been shown to have a defective proliferative response to MCSF, and fail to undergo MCSF-induced terminal differentiation (Serreze, et al. *J. Immunol.* 1993; 150:2534-2543). This led to speculate that autoimmune NOD mice lack a specific, MCSF-induced tolerogenic macrophage subset. The in vitro studies show that MCSF is a growth factor for both immunosuppressive and inflammatory macrophages, and that when inflammatory cytokines are present they act dominantly over MCSF. Thus, in the presence of dysregulated inflammatory cytokines, the addition of MCSF would be expected to exacerbate rather than reduce the disorder (Moore, et al. *J. Immunol.* 1996;157:433-440).

Based on the preliminary data, it was proposed that IFNγ induces IDO in certain macrophage and thereby triggers T cell suppression. This is a somewhat surprising role for IFNγ, which is generally considered pro-inflammatory rather than immunoregulatory. However, mice with targeted disruptions of the gene for either IFNγ (Krakowski, et al. *Eur. J. Immunol.* 1996; 26:1641-1646) or the IFNγ receptor (Willenborg, et al. *J. Immunol.* 1996; 157:3223-3227) demonstrate an unexpected hyper-susceptibility to experimental autoimmune encephalomyelitis (EAE). Mice normally resistant to this induced autoimmune disorder are rendered susceptible in the absence of IFNγ, and the disease is fatal and uncontrolled. Adoptive transfer studies showed that the requirement for IFNγ lay with an IFNγ-responsive regulatory cell, not with the autoreactive T cells. In contrast, these mice fail to mount an appropriate inflammatory response to intracellular pathogens (Dalton, et al. *Science* 1993; 259:1739-1742; Kamijo, et al. *J. Exp. Med.* 1993; 178:1435-1440). Thus, IFNγ is pro-inflammatory in infectious disease, but is immunoregulatory in at least one model of autoimmunity. This is consistent with the hypothesis that some macrophages respond to IFNγ as a signal to inhibit T cell activation.

The following examples demonstrate that 1-methyl-L-tryptophan, an inhibitor of L-tryptophan degradation, administered during murine pregnancy induces loss of allogeneic (mother and fetus are genetically different) conceptus 2-3 days after blastocyst implantation in uterus. Syngeneic conceptus are not affected by this treatment.

EXAMPLE 8

The mIDO Gene is Transcribed in Epididymis and In Conceptus During Pregnancy RT-PCR analyses on RNA extracted from a panel of mouse tissues was conducted to examine the extent of mIDO gene transcription in mice. mIDO transcripts were detected in RNA samples from mouse epididymis but not from muscle, heart, bone-marrow, spleen, peripheral lymph nodes, kidney, liver, brain, intestine or lung. PCR products were generated by RT-PCR amplification from RNA samples prepared from pooled syngeneic (s) or allogeneic (a) conceptus. RT-PCR amplification of murine α-actin transcripts was conducted on each RNA sample to verify RNA integrity. Methods: Female CBA mice were mated with syngeneic or allogeneic (B6) male mice. Females were inspected daily (am) for vaginal plugs; the morning plugs were detected was taken as 0.5 dpc (days post coitus). All conceptus dissected from each pregnant female were pooled, snap frozen on liquid nitrogen and used or prepare total RNA using standard procedures by homogenization in RNA-STAT 60 solution (Tel-TestB Inc.). Transcripts of the murine IDO gene (Habara-Ohkubo, et al., 1991 Gene 105:221-227) were detected by RT-PCR using forward (GTACATCACCATGGCGTATG, SEQ ID NO:1) and reverse (GCTTTCGTCAAGTCTTCATTG, SEQ ID NO:2) oligonucleotide primers which generated PCR products of the expected size (740 bp). RT-PCR conditions used were 48° C., 45 min./94° C., 2 min. (1 cycle); 94° C., 30 sec./58° C., 1 min./68° C., 2 min. (40 cycles); 68° C., 5 min. (1 cycle). PCR products were fractionated on a 1.5% agarose/TBE gel containing ethidium, bromide and were visualized by ITV fluorescence and images of gels were recorded as a digital bitmaps using a high definition digital fluorescence and images of gels were recorded as a digital bitmaps using a high definition digital camera. RT-PCR amplification of the murine α-actin gene (480 bp) was performed in parallel to verify RNA integrity.

In all cases, PCR products from the α-actin gene were detected indicating that RNA samples were not degraded.

IDO gene expression has been described in human placental trophoblast cells. To examine whether IDO transcription occurs during murine pregnancy, RNA samples were prepared from uterus and conceptus of pregnant mice at various stages of gestation. Female mice (CBA) were mated to syngeneic (CBA) or allogeneic C57BL/6 (B6) male mice and inspected daily for vaginal plugs. The morning the plug was detected was taken as 0.5 days post coitus (dpc). RNA samples were prepared from dissected components of conceptus; embryos, decidua (extra-embryonic trophoblast plus maternal uterus) and from uterus tissues. mIDO gene transcripts were detected in conceptus, but not uterus from syngeneic and allogeneic conceptus at early (7.5 dpc, 9.5 dpc) gestation times. mIDO transcripts were not detected in embryo RNA at 9.5 dpc suggesting that decidual tissues were the site of IDO expression in the conceptus. At later gestation times (10.5 and 13.5 dpc) mIDO transcripts were detected in allogeneic conceptus but not in syngeneic conceptus. RNA was prepared from decidual tissues dissected separately from embryos. mIDO transcripts were not detected in RNA from embryos at 10.5 or 13.5 dpc. From these data it was concluded that mIDO transcription occurs in decidual tissues of all conceptus from early gestation times (7.5-9.5 dpc).

EXAMPLE 9

Loss of Allogeneic Conceptus Occurs in the Presence of an Inhibitor of IDO Enzyme Activity A study was conducted to test whether IDO enzyme activity contributes to survival of fetal allografts by treating pregnant female mice with l-methyl-L-tryptophan, an inhibitor of IDO enzyme function. Female (CBA) mice were mated with syngeneic (CBA) or allogeneic (B6) male mice. On 4.5 days post coitus ("dpc") two slow-release pellets impregnated with 1-methyl-L-tryptophan (1 g/kg/day) were surgically implanted under the dorsal skin of pregnant mice. Control mice were treated with pellets not impregnated with 1-methyl-L-tryptophan (placebo groups). After surgery, mice were sacrificed and their uterus examined macroscopically and microscopically at various stages of gestation.

Based on comparison with extensive breeding records from the MCG Transgenic Unit fecundity rates for mouse colonies bred at MCG are 6.8 (CBA×CBA) and 6.4 (CBA×B6) pups per female at parturition. The same procedure was used to assess embryo survival and development in the mating combinations presented in Table 2. A large cohort of untreated female CBA mice mated with GK transgenic male mice were examined and are included in Table 1 to show that the mean number of conceptus (at parturition) is identical to the [CBA×B6] mating combination.

Results are summarized in Table 1.

TABLE 1

Inhibition of IDO activity induces rejection of allogeneic conceptus

| Mating Genotype conceptus ♀ × ♂ | Gestation Stage (dpc) | Mean No. conceptus/♀; (No. ♀ treated) | | Appearance of | |
|---|---|---|---|---|---|
| | | Inhibitor | Placebo | Inhibitor | Placebo |
| CBA × CBA | 6.5-8.5 | 7.3 (3) | 7.5 (2) | normal | normal |
| | 15.5 | 6.7 (6) | 6.5 (6) | normal | normal |
| CBA × B6 | 6.5 | 7.3 (3) | 8.5 (2) | normal | normal |
| | 7.5 | 4.5* (6) | 8.0 (4) | majority inflamed | normal |
| | 8.5/9.5 | 0.5* (17) | 7.3 (6) | all inflamed | normal |
| | 11.5-15.5 | 0* (7) | 5.8 (4) | — | normal |

*p < 0.05 by ANOVA compared to placebo controls at each time point

Treatment with 1-methyl-L-tryptophan had a profound affect on development of allogeneic conceptus. Syngeneic and allogeneic conceptus in mice treated with 1-methyl-L-tryptophan were found in normal numbers, were all healthy and were at the appropriate stage of fetal development at 6.5 dpc. Examinations conducted at 7.5 dpc, however, revealed striking differences in the numbers and appearances of conceptus. The average number of allogeneic conceptus+inhibitor was reduced to 4.5 per female at 7.5 dpc and declined to <2 at 8.5/9.5 dpc. No conceptus were present on any mice carrying allogeneic conceptus and treated with 1IDO inhibitor after 9.5 dpc. Normal numbers of healthy allogeneic (−IDO inhibitor) and syngeneic (±IDO inhibitor) conceptus were present in control groups. Methods. Mice were mated, treated with IDO inhibitor and dissected at gestation times indicated. Tissues were prepared for sectioning by fixing them in 4% paraformaldehyde. Serial sections (5 μm) were prepared using a microtome and were stained with hemtoxylin and eosin before microscopic examination.

On gross examination significant inflammation and excessive maternal blood surrounded the majority of 7.5 dpc allogeneic conceptus in mice treated with IDO inhibitor. In contrast, maternal blood was localized normally near the ectoplacental cone in all 7.5 dpc syngeneic conceptus treated with IDO inhibitor; their appearance was indistinguishable from that if syngeneic and allogeneic conceptus dissected from mothers in placebo groups.

On histological examination increased numbers of enlarged blood vessels within the decidual region were observed in 7.5 dpc allogeneic conceptus when IDO activity was blocked. However, allogeneic 7.5 dpc embryos appeared intact and at the expected developmental stage. One day later (8.5 dpc) allogeneic conceptus (+IDO inhibitor) were grossly abnormal. Extensive mixed mononuclear and neutrophil infiltrates were evident in every conceptus and were accompanied by extensive tissue degeneration in the decidual region. Grossly abnormal embryos were present but developmentally retarded. At 9.5 dpc no allogeneic embryos were present in mice treated with IDO inhibitor and decidual swellings were not apparent; some cellular debris was detected within the uterine lumen.

These data reveal that blocking IDO activity during pregnancy has a profound and specific effect on development of allogeneic conceptus, leading to loss of all embryos by mid-gestation. Embryo loss was not caused by surgical manipulations to implant pellets at 4.5 dpc. This data shows that blocking IDO activity compromises development of conceptus only when there is a genetic difference between mother and embryos. This implies that functional IDO enzyme activity is essential to protect allogeneic conceptus during early gestation and that the maternal immune system is involved in processes that lead to loss of allogeneic conceptus.

EXAMPLE 10

Maternal Lymphocytes Provoke Loss of Allogeneic Conceptus when IDO Activity is Blocked The contribution of maternal lymphocytes to experimentally induced loss of allogeneic conceptus in mice treated with 1-methyl-L-tryptophan was assessed using females carrying the RAG-1 induced mutation (RAG-1-/-) which prevents development of T or B cells (Li, 1982, Cancer 50, 2066-2073). As before, female mice carrying disrupted RAG-1 genes (on the DBA background) were mated with B6 males and treated with 1-methyl-L-tryptophan (4.5 cpd). Pregnancies were continued until 11.5 dpc when females were sacrificed to assess the number of conceptus. Normal numbers of healthy conceptus were found in all females examined (Table 2, first line).

TABLE 2

Maternal lymphocytes and a single MHC I alloantigen induce embryo rejection

| Mating Genotype No. (♀ × ♂) | IDO Inhibitor | No. ♀ examined (dpc) | Mean conceptus/♀ |
|---|---|---|---|
| CBA [RAG-1-/—] × B6 | yes | 5 (11.5) | 7.8 |
| CBA [RAG-1-/—] × B6 | yes | 2 (20.5, post partum) | 7 (pups born) |
| CBA × GK* | yes | 4 (11.5) | 0 |
| CBA × GK* | no | 21 (11.5) | 6.4 |

*GK mice are H-2K$^b$-transgenic mice made on the CBA background.

This data demonstrates that maternal lymphocytes are essential participants in events that precede loss of allogeneic conceptus when IDO activity is blocked. The most likely explanation is that maternal T cells are responsible for initiating mediating processes that lead to loss of allogeneic conceptus when IDO activity is blocked. This premise is based on the assumption that conceptus, like tissue allografts, provoke T cell responses. Although B cells, via antibody production, can contribute to allograft rejection, it is unlikely that antibodies against fetal alloantigens mediate rapid loss of conceptus a few days after implantation, especially as virgin females were used in these experiments.

EXAMPLE 11

A Single MHC 1 Difference Provokes Loss of Allogeneic Conceptus

B6 and CBA mice differ at a large number of genetic loci including the entire MHC region (MHC I and MHC II) as well as at multiple minor histocompatibility (miHC) loci. To determine whether a single polymorphic MHC molecule could provoke fetal loss, CBA mice were mated with (GK) transgenic male mice carrying a recombinant H-2K$^b$ (GK) transgene; a promoter from the human HLA-G gene drives H-2K$^b$-expression at high level in murine trophoblast (Zhou, et al. 1998 *J. Reprod. Immunol.* 40, 47-62). GK mice were made on the inbred CBA strain background and, hence, differ from CBA mice only because of H-2K$^b$ expressed by the GK transgene. Normal size litters are borne by CBA females after mating with GK transgenic male mice (Table 2). Pregnant mice were treated with 1-methyl-L-tryptophan and examined at 11.5 dpc, as before, to assess effects on fetal development (Table 2). No conceptus, nor any resorbed decidua, were observed when mice were examined on 11.5 dpc, although, in each mouse, the uterus was distended indicating that pregnancy had terminated prematurely.

This result is important for two reasons. First, a single paternally-inherited MHC I difference between mother and conceptus is enough to provoke fetal loss when IDO activity is blocked. Second, it eliminates the possibility that fetal loss occurs after CBA [×B6] matings because of an inherent genetic predisposition to fetal loss in this mating combination.

This result supports the view that maternal T cells, not B cells, are responsible for fetal loss since MHC alloantigens provoke strong T cell responses but weak B cell responses. If true, this implies that maternal CD8$^+$ T cells recognizing native H-2K$^b$ molecules expressed by fetal cells may be responsible for provoking fetal loss.

In summary, these data demonstrate that the IDO enzyme inhibitor 1-methyl-tryptophan has a profound and specific abortifacient effect on all allogeneic conceptus prior to 9.5 dpc. Fetal abortion is not due to non-specific toxic affects of the drug itself as syngeneic conceptus develop normally in females exposed to 1-methyl-tryptophan as do allogeneic conceptus in the absence of maternal lymphocytes. Alternatively, embryonic development may be affected by substances produced when 1-methyl-tryptophan is metabolized by cells expressing IDO. However, this is unlikely to explain the abortifacient effect of 1-methyl-tryptophan since the IDO gene is expressed in syngeneic and allogeneic conceptus early in gestation during the period when embryo rejection occurs (7.5-9.5 dpc). One therefore concludes that the abortifacient effect of 1-methyl-tryptophan arises because it inhibits IDO enzyme activity. Decidual cells expressing IDO normally establish a protective barrier that prevents maternal T cell mediated rejection of allogeneic conceptus.

EXAMPLE 12

Inhibition of Tumor Growth by Administration of IDO Inhibitor

In light of the data herein showing that the allogeneic fetus is able to protect itself against attack by the maternal immune system through expression of IDO, and given the expression of IDO in tumors as cited above, it was tested whether a similar mechanism allowed tumor cells to evade immune attack. The MB49 epithelial carcinoma model was chosen for proof of concept because it is an aggressive, lethal malignancy when innoculated into syngeneic hosts, but it can be rendered susceptible to immune attack if the host's immune system is suitably activated (Chen, et al. 1997 *J. Immunol.* 159, 351-359). Tumor-bearing hosts were treated with the IDO inhibitor 1-methyl-tryptophan. MB49 tumor cells ($1\times10^6$) were injected subcutaneously into syngeneic C57/B16 hosts. Pellets containing 1-methyl-tryptophan (0.9 mg/hr, 7-day release) were implanted at the time of tumor cell innoculation. By day 10, all animals had evidence of initial tumor formation (palpable mass). By day 15, control animals were visibly ill and the experiment was terminated. Animals were sacrificed on day 11-15 for histologic examination.

As shown in Table 3, administration of 1-methyl-tryptophan significantly reduced tumor growth in immunocompetent, syngeneic hosts, compared to vehicle control. Two important points are noted: First, no manipulation of the immune system other than inhibition of IDO was required for anti-tumor effect—i.e., the tumor itself became immunogenic once the barrier of fDO was removed. Second, the observed responses continued at least 4-7 days after the period of inhibitor administration (days 1-7), suggesting that an initial priming period was sufficient to generate a sustained anti-tumor immune response.

TABLE 3

Anti-tumor effects of 1-methyl-tryptophan administration.

| Outcome measure | control group (n = 7) | 1-methyl-tryptophan group (n = 7) |
|---|---|---|
| complete responses | 0 | 1 |
| partial responses | 0 | 6 |
| size of residual tumor | 2-2.5 cm | 1 cm (necrotic) |
| histology (day 15) | viable tumor, minor infiltration of CD4+ T cells with occasional CD8+, scattered macrophages | apoptosis, necrosis, and hemorrhage, extensive infiltrate of CD4+ and CD8+ T cells, extensive infiltration of macrophages |
| visible metastases | extensive local metastases, with gross evidence of intraperitoneal and visceral metastases | none |
| performance status | decreased activity, failure to groom, ill appearance | normal |

Modifications and variations of the methods and compositions described herein will be obvious to those skilled in the art and are intended to be encompassed by the claims.

---

We claim:

1. A pharmaceutical composition for altering extracellular tryptophan concentrations comprising an effective amount of 1-methyl-tryptophan suitable for administration to a patient in need of treatment thereof to alter extracellular levels of tryptophan to modify T cell mediated immunity, and a pharmaceutically acceptable carrier for administration to a patient, wherein the pharmaceutical composition is formulated in a tablet or capsule.

2. A pharmaceutical composition comprising 1-methyl-tryptophan and a pharmaceutically acceptable carrier, wherein the pharmaceutical composition is formulated in a tablet or capsule.

3. A pharmaceutical composition comprising 1-methyl-tryptophan and a pharmaceutically acceptable carrier, wherein the pharmaceutical composition is formulated for enteral administration and for controlled or sustained release.

4. A pharmaceutical composition comprising 1-methyl-tryptophan and a pharmaceutically acceptable carrier, wherein the pharmaceutical composition is formulated for enteral administration.

5. The pharmaceutical composition of claim 4 wherein the pharmaceutical composition formulated for enteral administration is a tablet or capsule.

6. The pharmaceutical composition formulated for enteral administration as a capsule or tablet of claim 5 wherein the capsule or tablet is enteric coated.

7. The pharmaceutical composition formulated for enteral administration as a capsule or tablet of claim 5 wherein the capsule or tablet is formulated for controlled or sustained release.

* * * * *